US012040073B2

(12) United States Patent
Holen

(10) Patent No.: US 12,040,073 B2
(45) Date of Patent: Jul. 16, 2024

(54) METHOD FOR RESOLVING GENERALIZED AND TRAUMA RELATED ANXIETY

(71) Applicant: Scott Holen, Bellingham, WA (US)

(72) Inventor: Scott Holen, Bellingham, WA (US)

(*) Notice: Subject to any disclaimer, the term of this patent is extended or adjusted under 35 U.S.C. 154(b) by 615 days.

(21) Appl. No.: 17/060,057

(22) Filed: Sep. 30, 2020

(65) Prior Publication Data
US 2021/0098111 A1 Apr. 1, 2021

Related U.S. Application Data

(60) Provisional application No. 62/908,426, filed on Sep. 30, 2019.

(51) Int. Cl.
G16H 20/70 (2018.01)
G16H 80/00 (2018.01)

(52) U.S. Cl.
CPC ............ G16H 20/70 (2018.01); G16H 80/00 (2018.01)

(58) Field of Classification Search
CPC ............................ G16H 20/70; G16H 80/00
See application file for complete search history.

(56) References Cited

U.S. PATENT DOCUMENTS

| 2002/0091307 A1* | 7/2002 | Kanter | A61B 5/16 |
| | | | 600/300 |
| 2006/0204937 A1* | 9/2006 | Grignon | G09B 19/00 |
| | | | 434/236 |
| 2008/0213736 A1* | 9/2008 | Morris | G09B 7/02 |
| | | | 434/236 |
| 2010/0021874 A1* | 1/2010 | Cunningham | G09B 19/00 |
| | | | 434/238 |
| 2010/0196862 A1* | 8/2010 | Frischer | G09B 19/06 |
| | | | 434/167 |
| 2014/0120508 A1* | 5/2014 | Jensen | G09B 19/00 |
| | | | 434/236 |

(Continued)

OTHER PUBLICATIONS

Dark Daily, "FDA Approves Digital Therapeutics Technologies to Treat Patient Behavioral Conditions That Interfere with Positive Healthcare Outcomes", Jan. 27, 2020, 4 pages.

(Continued)

Primary Examiner — Gary Collins
(74) Attorney, Agent, or Firm — Puget Sound Patents; Dwayne E Rogge

(57) ABSTRACT

A process for reprogramming the responses of a subject to external stimuli. During the process, the subject identifies a personal negative belief—or automatic negative response to an external stimulus—and identifies a plurality of negative terms that strongly correlate, in the subject's mind, with the belief. For each of the negative terms, the subject expands upon the correlation, exploring the emotional effect or personal feelings aroused by the correlation of each of the terms with the belief. The subject then identifies an appropriate alternative belief and correlates the appropriate belief to each of a plurality of positive terms, then then expands and explores the personal feelings or emotions aroused. The subject then evaluates any change resulting from the process. The subject may repeat the process while selecting a new negative belief, or with the same belief as before, in one example with a different plurality of negative terms.

20 Claims, 18 Drawing Sheets

(56) References Cited

U.S. PATENT DOCUMENTS

2014/0223462 A1* 8/2014 Aimone ............ H04N 21/4307
725/10

OTHER PUBLICATIONS

David Forbes et al., "Effective Treatments for PTSD, Practice Guidelines from the International Society for Traumatic Stress Studies" (558 pages), Chapters 6, 7, 11, 12, 13, 14, 15, and 18, 2020, 146 pages, The Guilford Press, New York, NY.

Digital Therapeutics Alliance, "Digital Therapeutics: Combining Technology and Evidence-based Medicine to Transform Personalized Patient Care", Oct. 2018, 16 pages.

Hogan Lovells, "Digital Health, Leverage its full potential in 2018, Global Life Sciences and Health Care", 2017, 64 pages.

* cited by examiner

METHOD FOR RESOLVING GENERALIZED AND TRAUMA RELATED ANXIETY

CROSS-REFERENCE TO RELATED APPLICATIONS

This application claims the benefit under 35 U.S.C. § 119(e) of U.S. Provisional Patent Application No. 62/908,426, filed Sep. 30, 2019, which provisional application is incorporated herein by reference in its entirety.

BACKGROUND

Field of the Invention

The present invention relates to methods and software programs for treating stress induced anxiety and trauma related syndromes, such as chronic anxiety and PTSD, and, more particularly, to the treatment and reprogramming of undesirable responses to environmental stimuli.

Related Art

PTSD (post-traumatic stress disorder) is a definable anxiety condition arising from the inability to naturally resolve internal stress, over reasonable timeframes, caused by external crisis or trauma as defined by the individual. PTSD is characterized by post-event chronic, implicit, and automatic emotional responses to certain seemingly benign referential stimuli as though to the original trauma. These automatic responses can be seen as positive, in the attempt to protect the central nervous system from additional random unresolvable stressors; negative by way of unnecessary avoidant behaviors and emotion flooding. Such automatic negative behaviors tend to reinforce learned helplessness to everyday effecting stimuli, thereby limiting the ability to thrive at higher personal and social levels. It is well documented that generalized anxiety, and the more severe PTSD can drastically reduce quality of life through unmanageable, strong, and sometimes violent emotions, and can render a sufferer incapable of sustaining normally functioning relationships, holding a job, interacting with family members, etc.

DETAILED DESCRIPTION

Figure 1:
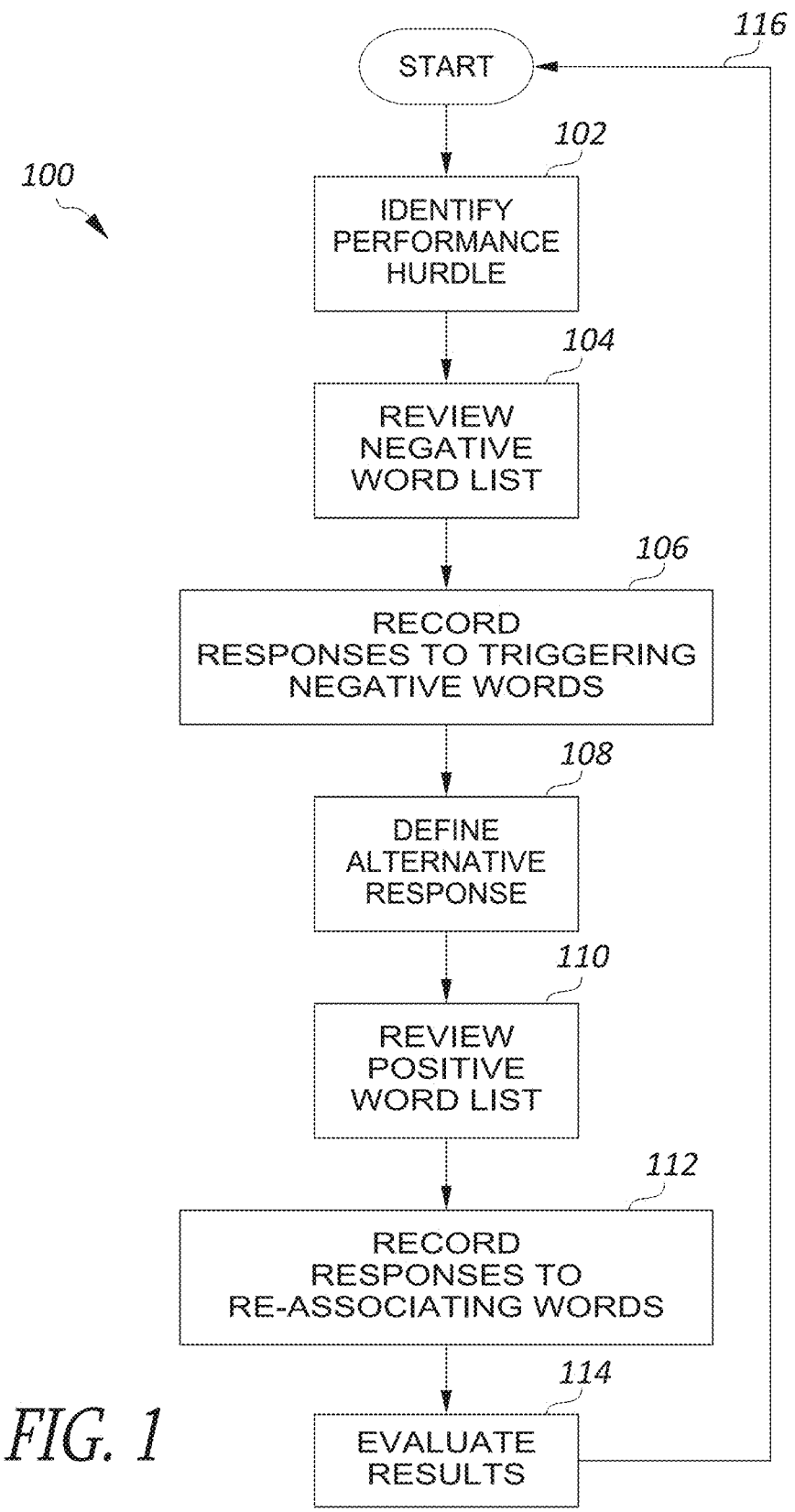
FIG. 1 is a flow chart illustrating a process for the resolving of generalized and trauma related anxiety, according to an embodiment.

Efforts to help those suffering from internal emotional challenges lending to discomfort and suboptimal life and interpersonal experiences, have generated a large number of modalities developed for the treatment of generalized anxiety and PTSD, with varied results. In general, modalities designed to modify performance at the conscious or cognitive level focus on an identifiable painful event or chronic underperformance difficulties, and primarily fall under the category of Cognitive (conscious thought) Behavioral Therapy (CBT). Such modalities use the approach of new cognitive learning or mindfulness to act as a buffer or thoughtful defense from ongoing or daily stressors, and to mitigate distorted thoughts and negative performance as a result of chronic unresolved stress. Some of the most widely practiced CBT modalities include: Cognitive Therapy (CT), Cognitive Processing Therapy (CPT), Exposure Therapy (EX), Written Exposure Therapy (WET), Stress Inoculation Training (SIT), Relaxation Training (RLX), Dialectical Behavior Therapy (DBT), and Acceptance and Commitment Therapy (ACT).

A significant portion of CBT treats the symptoms of performance hurdles in the conscious while failing to modify the root aspect of unresolved or poorly encoded past experiences residing in the subconscious. For effective treatment of generalized anxiety and more definable and embedded PTSD, a resolution to an expressed performance hurdle, by means of new cognitive learning based on a close examination of a perceived inducing event, accepts the perceived permanence of the underlying condition, while building workarounds or making the most of the accepted condition rather than resolving the error in encoding (act of storing experiences as memories) that is understood to be the underlying source or driver of the hurdle.

In addition to the referenced clinically studied CBT modalities there are certain significant modalities widely used to help a person reduce anxiety under the theory that working at the subconscious or non-cognitive level will automatically reduce anxiety and improve behavior without a cognitive learning aspect. These processes work to bypass psychological fear structures built as a result of unresolved crisis or trauma, attempting to boost the natural mechanisms that operate to resolve prior negative experiences and improve the prior attempts at associative encoding which is the brain's natural function (storing memory by association rather than chronologically). Examples of modalities that fall under this category are: Eye Movement Desensitization and Reprocessing (EMDR), Emotional Freedom Techniques (EFT), and Hypnosis. Embodiments disclosed and described herein align more (in general) with this second category.

The embodiments disclosed are believed to be more precise in nature, allow a pinpointed access to the subconscious, support capture of poorly encoded disruptive memories, release them to be more positively encoded, simultaneously improve performance potential, all while addressing the problem of chronic unresolved stress under theories for reengineering neuro pathways and current understanding on neuroplasticity, while allowing for a cognitive component in relation to concluded and associated feelings.

Most of the modalities of treatment of chronic anxiety disorders, including PTSD, include one or more of the following characteristics: they require outside intervention by mental health professionals, can take numerous sessions to obtain effective resolution and, in extreme cases of significant trauma, can require an individual review in painful detail, the event(s) that provoked the condition in the first place, typically many times over, at great personal and financial cost, before visible results are shown.

Many individuals, particularly those whose performance hurdles are rooted in trauma that was experienced early in life, can have the added complication of having partially or completely repressed their memories of the original event(s). This increases the difficulty of treatment by means of standard Cognitive Behavioral Therapies.

Because of the associated cost and time requirements, many individuals suffering from chronic anxiety disorders don't have the personal resources or support necessary to obtain effective treatment, and that even among those who do have access to treatment, many are unable to find a comprehensive solution.

PTSD is a dysfunction in the encoding and retrieval process of the subject's memory in relation to extremely surprising and oftentimes painful negative stimuli and the associated thoughts related to the stimuli, in context to prior learning and a mercurial sense of personal value or worth. In an average person under normal circumstances, the subconscious is continually evaluating and correlating incoming stimuli and prompting responses based on past responses to similar stimuli. In the case of negative stimuli, the current responses are based on previous responses that may have been effective in avoiding, or at least mitigating the effects of similar or associated stimuli of the past. Thus, a subject's behavior in response to a particular stimulus is often based on the sum of many uniquely personalized prior responses to similar stimuli. Under more difficult circumstances, and when these responses are negative and/or personally damaging (harmful, traumatic), the level and speed of downward spiraling emotions can increase anxiety and avoidance, lending to (tending toward) a cycle of increasing suboptimal performance. From the point of view of the individual, these responses can be effectively automatic or reflexive in nature, bypassing conscious control and becoming what might be viewed as elements of the subject's established character or personality.

For example, one person might tend to respond to particular situations with anger and avoidance, while another might respond to similar situations with empathy and patience, according to programming that may have begun in early childhood, and that often appears to be beyond the conscious control of the subject, at least by the time the subject is a teenager or adult. The process of programming the subconscious, however, can be extremely subtle, making it difficult to modify behavior, in an adult, that is rooted in childhood and beyond. This can be the case where the memories of some or all the events that originally prompted the behavioral programming have become lost over time, so that the subject is not able to identify the basis for the behavior. When automatic responses impact the individual's external environment in a disharmonious manner or at a conflicting tangent to the individuals expected internal and external environmental experience this can lead to an anxiety of a type that is akin, albeit to a lesser degree, to the anxiety experienced by someone diagnosed with PTSD. The difference, in a sufferer of PTSD, is one of scale rather than type.

If this is true, that there is an amnesiac state to the memories related to a person's anxiety, or that a subject's response to a particular stimulus may be internally programmed as a general response, anything associated with a long chain of stimuli and consequences extending into the subject's past, much of which the subject no longer has conscious memory, then it raises a particular problem, when considered in the context of resolving the impact that PTSD, as well as what impact generalized anxiety has on a person's internal and external performance: In most cases of PTSD, a subject might be able to identify a particular traumatic event or events apparently responsible for programming the disruptive conditioned response, but the conditioned response may in fact include components initiated by many prior, though far less traumatic events, most of which are effectively lost to the subconscious or otherwise forgotten by the subject, and too remote in time to be identifiable by other means. Thus, treatment of the conditioned response may be unsuccessful or inadequate if therapy is limited to the consideration of a single event, or a definable series of extremely difficult cognitive events, while ignoring the secretive non-cognitive history.

This is an even greater problem in the treatment of more generalized anxiety, inasmuch as there may be no identifiable basis or explanation for its genesis. To effectively treat generalized anxiety and more definable and embedded PTSD at a purely cognitive level may instead require the examination of a string of events and decisional patterns possibly going back into the subject's childhood—due to the associative storage processes of memories—many of which would have no obvious cognitive connection or correlation with an event identified as the basis for a case of PTSD, because of the universal functionality of the human brain. On the other hand, a treatment that is effective in addressing PTSD may also be effective in reprogramming a subject's conditioned negative responses to common stimuli, even if the subject has never had, or been diagnosed with PTSD.

Society assigns positive or negative value to a person's behavior in response to a given situation. Subconsciously, an individual tracks his or her own value in the same way. To the extent that a person's programmed responses have a negative social value, such as, e.g., anger, scorn, fear, denial, procrastination, passivity, avoidance, etc., the subconscious associates a negative personal value with the negative responses, meaning that a person's personal value is measured by the sum of the values assigned to each of the programmed responses. The converse is also true: responses with positive social values are also part of this internal calculus, with corresponding positive impacts on the sum.

A person suffering from PTSD may have many different programmed responses, ranging, for example, from rage to resignation, depending upon the specific stimulus. The stimulus can act as a trigger to provoke a response that was programmed to cope with a poorly resolved original stimulus, then reinforced by responses to subsequent stimuli. A person's responses to stimuli can be reprogrammed, whether the subject suffers from PTSD or merely wishes to modify personal behaviors and reactions that are unproductive and prevent one from realizing goals and higher levels of satisfaction in life in general. Further, specific behaviors are born out of specific conscious and subconscious drawn conclusions (established associations), whose building blocks may be associatively nestled experiences (memories) that become, a tangible object or tangible construct of neurotransmitters that remain in place and stay at rest in that state until a specific force is applied to it. Re-associating or response reprogramming can be done thru specific and formulaic steps to identify instances of negative or fearful association stuck in a negative or poorly encoded fear state and allow for re-association under safe and reasoned conditions.

This re-association effort releases prior downstream subconscious negative associations and allows for positive ones without having to retraumatize the subject through specific, painful, or difficult memory re-examination. Rather than attempt to reconcile an individual to past traumatic events, the response to those events can be used to identify where in the associative collection of experiences (memories) result in a negative emotional response or behavior allowing for modification, which can improve the self-worth of the individual as well as the perceived value of that individual by others. Reconciliation to an original event follows as a natural byproduct of the reprogrammed responses and the resulting improvement in self-worth. The subject perceives that the reverberating effects or reminders of the original event are perceptibly diminishing over a relatively short period, as the subject addresses each performance hurdle in turn.

FIG. 1 is a flowchart illustrating a process 100 for reprogramming the responses of a subject to external stimuli, according to an embodiment. The process does not require the presence, direction, or intervention of a mental health professional, and can be done at the subject's home, or any other convenient location. However, there might be situations in which a coach is advantageous in helping the subject progress most quickly and effectively. It may also be beneficial for a subject to have help identifying the behaviors that are viewed as having negative social value, and the circumstances under which such behaviors are expressed by the subject, and also for providing an objective analysis of the effectiveness of the process with that subject.

At step 102, the subject first identifies a single personal and specific performance hurdle, i.e., a performance goal or objective that the subject is unable to achieve, an inappropriate and automatic response that the subject is unable to control, or an anchored negative belief perceived to be blocking the achievement of specific goals, etc. For example, the subject might identify "I struggle to control my anger," "I treat my wife badly when we argue or disagree," or "I can't stop being startled by unexpected and loud noises" as a common performance hurdle or negative personal response that is largely undesirable.

The subject then, at step 104, goes through a list of words that characterize negative conclusions or negative feelings that may arise from or be associated with the performance hurdle. Such a list might include, for example, nonexistent, invisible, empty, lonely, wounded, tormented, disgusting, spoiled, selfish, arrogant, controlling, etc. These words can be thought of as representations of possible underlying drawn conclusions or neurotransmitter clusters established as a result of fearful or negative encoding of prior experiences. For each triggered conclusion or feeling, in step 106, the subject records a brief personal response relating the word and the target performance hurdle. For example, the subject might record: "I feel selfish when I respond in anger to a simple and innocuous comment by my wife." In most cases, a number of the listed feelings or potential trigger words will resonate strongly with the subject and may trigger or activate memories, both conscious and subconscious, responsible for the lack of energy or ability to overcome the target performance hurdle, prompting a more detailed or extensive explanation. On the other hand, with others of the listed feelings or suggested trigger words, the subject may feel no particular reaction, in which case, the response can be blank or very brief, indicating the absence of a negative drawn conclusion around the struggle to overcome the target performance hurdle.

The list of terms may include, for example, 1 to X (where X is a positive integer) separate terms that may be associated with negative feelings that occur in response to negative or inappropriate behavior.

While steps 104 and 106 are described as being performed in sequence, the subject will, in most cases, interleave the steps, i.e., review a first word from the list of words, in step 104, associate that word with the selected performance hurdle and record any thoughts or emotions that arise from the association, in step 106, then return to step 104 and review a second one of the words, return to step 106 an associate the word with the performance hurdle, and so on through the list of words, before moving on to step 108.

In step 108, the subject internally identifies a desired alternative goal response that has a positive social value and can substitute for the expressed performance hurdle. For example, as a substitute for "I struggle to control my anger," the subject might identify: "I have boundless patience," or "I respond with equanimity to obstacles," as a more appropriate and socially positive goal response. In step 110, the subject then reviews a second list that includes a series of positive terms defining conclusions or feelings that might be associated with the less anxious, more positive goal response. Such a list might include, for example, terms such as caring, compassionate, supportive, understanding, engaged, determined, honest, trustworthy, loving, etc. In step 112, as in step 106, for each of these listed trigger/activation words, the subject records a brief personal response relating or associating the listed emotion and the goal response. For example, the subject might record, "I feel trustworthy when I respond with patience to a coworker who says something that could be interpreted in a negative way."

At step 114 the subject evaluates the results of the exercise. Finally, at step 116, the subject repeats the process 100, as needed, identifying a new performance hurdle that has a negative social value, and introducing an alternative response with a positive social value. It is not necessary that the subject repeat the process for the same performance hurdle to establish relief, but additional iterations of the same hurdle can speed the process of reassociation. It is also not required that the subject perform additional processes with different performance hurdles in order to obtain relief in the first.

In one example the process can only be performed by the individual whose behavior is to be modified. Thus, use of the term personal, in the claims, denotes the performance of the process by that individual.

In steps 104 and 106, the exercise reaches into the subconscious, identifies fear structures and negative drawn conclusions that are blocking the performance of the desired achievement, as they relate to the identified performance hurdle, and makes them available for change. While the memory or memories are subconsciously activated thru the relationship they have with a person's subconscious or now cognitively recalled negative drawn conclusion(s), they remain available for a period, to be re-considered and encoded while released from prior negative associations and in a manner less likely to cause triggering and avoidance.

Over the course of this part of the exercise, the subject may be priming the subconscious to seek alternative behaviors, through recognition that the performance hurdle engenders negative feelings of its own, every time it is expressed.

In the second part of the exercise, i.e., steps 108, 110, and 112, the conscious and subconscious parts of the brain recognize previous instances where positive conclusions and behaviors have been achieved when encoding and memory associations have been more successfully positive, and opens the subject to positive alternatives. By recognizing and allowing for a decisioned change in association, the brain, thru its natural functioning, re-associates the effects or interpretations of prior difficult or painful memories that may have been unavailable to the subject prior to working the process. This is done thru the subject's ability to establish a more reasoned and rational alternative conclusion to personal value and strength of determination in relation to the selected performance hurdle, organically altering behavior as a natural by-product.

One embodiment of the process 100 has been practiced with subjects. Evaluation of the process and its efficacy by the various subjects suggests that the process is an effective tool in treating generalized anxiety, even to the level of complex PTSD, and reducing dread associated with being stuck in negative behaviors or the inability to achieve personal goals. In many cases, negative behaviors were reprogrammed almost immediately. Testing of prior known methods through roughly five full years of professional therapy over a span of twenty total years for PTSD related symptoms without significant improvement in comparison to the practice of the process 100 disclosed herein, the inventor was able to accomplish, very quickly, what had been previously impossible, even with extended therapy. This is a very surprising result, given the extensive professional therapy that had produced minimal results, and the fact that the inventor is not a mental health professional. This is also surprising, in a broader sense, in that the case study results demonstrate that an individual can, via a process such as that disclosed above, and with little or no professional guidance, obtain results that far exceed any results that might reasonably be expected from a more conventional process that includes submitting to years of expensive treatment by mental health professionals.

Figure 2:
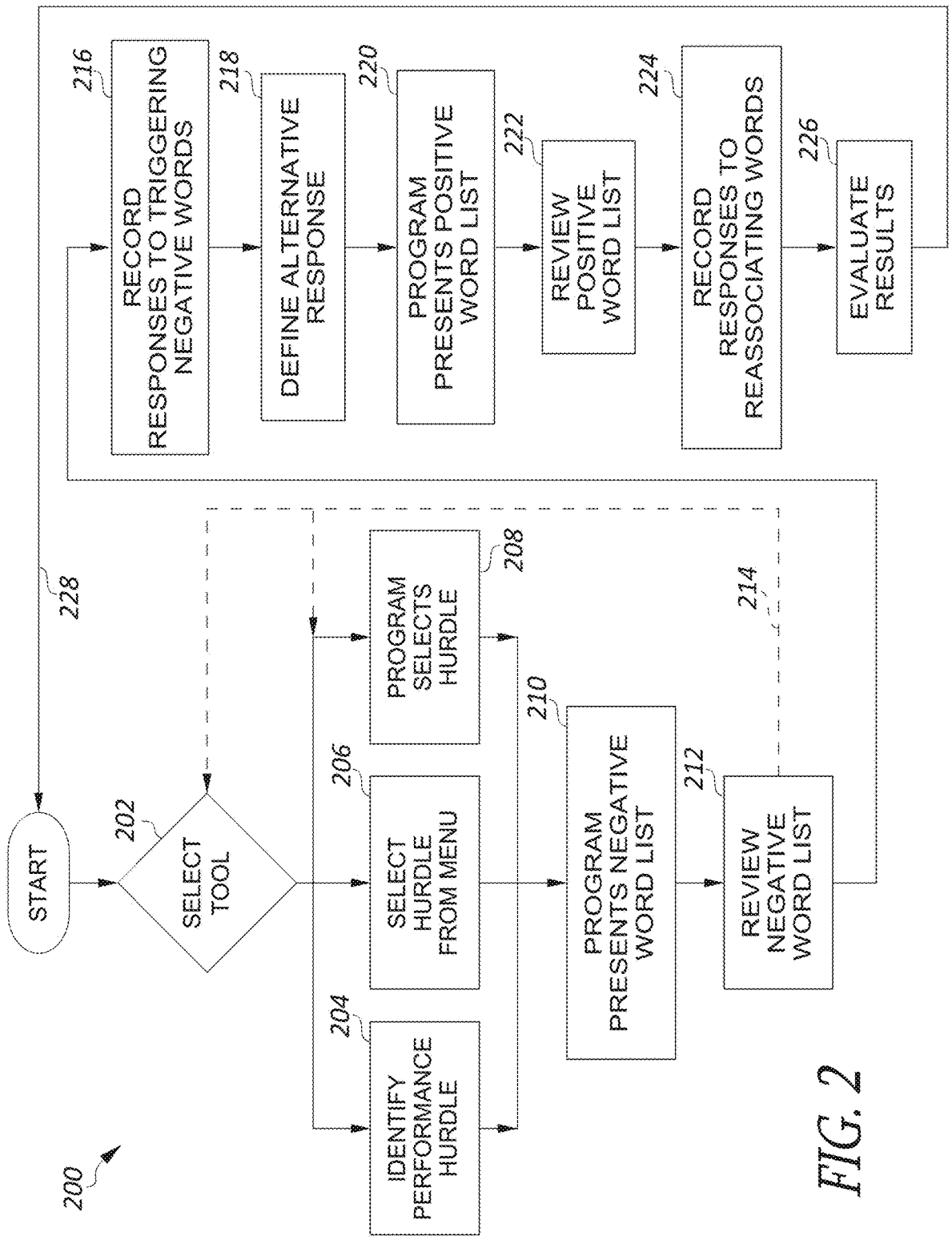
FIG. 2 is a flow chart showing a process stored on a non-volatile memory, for the resolving of generalized and trauma related anxiety, according to an embodiment.

FIG. 2 is a flowchart illustrating a process 200 for reprogramming the responses of a subject to external stimuli, according to an embodiment. Instructions for executing the process 200 are stored on a non-transitory computer-readable medium, for implementation using a general-purpose computer, according to an embodiment. The term general purpose computer includes within its scope digital computing devices such as smart phones, tablets, PDAs (personal digital assistants), smart watches, or other interactive electronic devices, etc. According to various embodiments, a subject can access the process 200, in the form of a software program or application ("app") via any of: a local drive or storage device, a cloud-based storage location, a removable drive, a third-party server, and/or web-based application, etc. Where the description of the process 200 refers to an action performed by the program, this can be understood as reference to an action performed by the general purpose computer or a peripheral thereof, in accordance with and in response to instructions stored as part of the process 200 and implemented by the computer or electronic device.

At step 202, the subject selects a tool, from among a plurality of options, for identifying a specific personal performance hurdle. According to an embodiment, the options include: step 204, in which the subject records a self-defined performance hurdle they want to overcome, or behavior they would like to change; step 206, where the subject chooses a suggested performance hurdle from a drop-down list organized into various predefined categories; or step 208, in which the program presents a random hypothetical situation found in everyday life that includes a typical or common performance hurdle. Once a performance hurdle is identified at one of steps 204, 206, or 208, the program presents, in step 210, a list of words generally linked to negative emotions and are presented for review by the subject. These are negative word which represent negative conclusions that possibly trigger a strong emotional response in the subject, when considered in relation to the performance hurdle. In step 212, the subject internally examines or explores the emotions provoked in response to the review of any triggering word and its association to the selected performance hurdle. As the subject reflects on each triggering negative word with the associated performance hurdle, and identifies corresponding emotional responses or memories, the subject records, in step 216, a description of the resulting responses and/or memories. In practice, the subject will generally interleave the performances of steps 212 and 216, as described above with reference to the embodiment of FIG. 1.

At any point while performing steps 212 and 216, the subject has the option to add to or change the listed negative words to find words that trigger an identifiable response. According to an embodiment, the subject can request additional words, which the program then supplies. If, while performing steps 212 and 216, the subject finds that the selected performance hurdle, with the corresponding word list, does not tend to provoke emotionally charged responses, the subject can return, via path 214, to any of steps 204, 206, or 208, in order to obtain a different performance hurdle, with its corresponding list of associated negative emotions.

At step 218, in relation to the specific performance hurdle identified in either step 204, 206, or 208, the program prompts the subject to internally consider a new behavior that has a positive social value and that the subject would like to substitute for the expressed performance hurdle, as the desired appropriate alternative. According to an embodiment, the program provides a list, in step 220, of positive, alternative feeling words or responses that might be associated with the selected alternative behavior in contrast to the list of negative words supplied in step 210. Then, at step 222, the program instructs the subject to review or internally explore the personal feelings for each provided positive word, in a manner similar to that described with reference to step 212.

In step 224, the program prompts the subject to record a description of the emotions 350 and/or memories that arise when considering each positive word and their relationship to the possibility of achieving the alternative behavior as related to the performance hurdle identified in any of steps 204, 206, or 208. According to an embodiment, the program may provide an example at each positive word to assist the subject in describing their individualized feelings. For example, the program might provide a partial phrase for the word "empathy" that the subject can adapt or complete, such as, "When I respond with empathy to _, I feel useful, because _. The subject can complete the phrase by filling in the blanks or modifying the selected phrase to more closely describe the subject's actual feelings in those circumstances. Alternatively, the subject might choose to ignore the example and enter a new phrase.

In step 226, the subject may evaluate the results of the entire exercise and the potential for long-term change. According to an embodiment, the program provides instructions for this step, describing, for example, various behaviors, feelings, and impressions that the subject can observe that offer clues to the outcome of the process. Following step 226, the subject returns, via path 228, to the beginning and begins a new iteration of the process 200 again, selecting a different performance hurdle.

According to an embodiment, the program also provides educational and mental healthcare information to provide subjects with information on self-care and available resources, etc.

Part of the effectiveness of the process comes as a result of the subject taking time, in step 224 and 226, to mentally review or contemplate in retrospect the process and the feelings engendered. This step supports the solidification or completion of re-associations, perhaps similar to, and supported by brain functionality and what is done each night while we sleep. At step 226 the subject evaluates the results of the exercise before proceeding to step 228. It is not necessary that the subject repeat the process for the same performance hurdle to establish relief, but additional iterations of the same hurdle can speed the process of reassociation. It is also not required that the subject perform additional processes with different performance hurdles in order to obtain relief in the first.

When the subject encounters a situation that would have elicited a negative behavior, they find that the baseline behavior does not occur automatically. Instead, the subject is able to recognize the circumstances, and choose to engage in an alternative behavior, where previously the behavior would have been automatic, so that recognition may have occurred after the negative behavioral response, if at all. re-associations correct themselves and stabilize in short order and in direct correlation to the subject's desire for change. Over time, the subject consistently chooses the alternative behavior more naturally at each iteration of the process of the challenge phrase or version thereof. The alternative behavior can become ingrained or embedded to the point of becoming at least the considered response, and eventually the automatic response rather quickly compared to other methods of change.

According to an embodiment, a purpose of the process 200 is to identify performance hurdles, including difficult-to-alter behaviors, and trigger the subconscious memory associations related to the heightened internal response and make them available for reassociation.

For example, at step 202, a hypothetical subject realizes their daily work commute has become more and more difficult to deal with. With each passing month they dread driving to and from work to an increasing degree and have arrived at a point where they consider quitting their job. As described above at step 204, the subject can phrase a performance hurdle in many different ways, such as, for example, "my commute is driving me crazy," "my commute is causing more and more anxiety each day," or "I can't stop being agitated by my daily commute." The exact phrasing is open to personal preference or nuance by the subject. A single iteration of the process 200 can be performed using one phrase, or multiple versions of the phrasing can be used in respective iterations of the process, depending upon what the subject finds in their realized responses in step 216 of the first iteration. Once the subject has established the phrasing and sentence structure of their performance hurdle, in step 204, the program transitions to lists of negative emotion words in step 210 for the purpose of identifying triggers or subconscious associations related to the relationship between driving and increased anxiety. These personally identified hurdles may be possible feelings of being trapped, held back, being on display, 410 fear of crowds or any number of associations for that specific individual.

As the subject associates the performance hurdle with each of the negative words, in step 212, the brain files thru the subject's subconscious memories in rapid fashion, pulling the relative historical pieces from their past that make up the associative neurotransmitter constructs generating their increasing anxiety, making the constructs available to be re-associated in a more positive frame of reference. As the subject comes to the negative word "trapped", for example, they might have a flash of memory related to being trapped in an elevator for a short period several years prior. In conjunction to the increase in traffic that is flooding them with similar feelings they had while stuck in the elevator, an associated memory trigger at the word "impacted" reminds them of an auto accident they had three summers prior in a collision with a blue Ford Mustang. At that point they may or may not realize on a conscious level that a similar Ford Mustang had joined the same commute route six months prior and has been subconsciously triggering the painful memory of the auto accident without realizing it. As the subject continues on with reviewing negative emotion words, they find themselves triggered by the word "undervalued" and it brings up the association of their new supervisor they dread seeing each morning because the supervisor has complained about the subject being late more often lately, which the subject knows is all related to their commute dread. This interaction with their new boss compounds or adds to the anxiety of the commute and the subject finds themselves at a tipping point of drastic downward spiral.

Once the subject has recorded their consideration on reasons for certain negative word triggers during the first half of the process in step 216, they are ready to proceed to the re-association half of the process by defining an alternative response to the performance hurdle in step 218. With these negative associations brought to a cognitive awareness and or internally identified in the subconscious, they are now available for reassociation through the reversal process via consideration of positive words supplied at step 220 and reviewed at step 222. This step in the process allows the subject to cognitively re-associate with more reasonable and balanced experiences. For example, As the hypothetical subject comes to the word survivor, the subject realizes that even though they were in an accident three summers prior they survived well and have thrived physically after a short time of physical therapy. As the process moves the subject from negative to positive emotion words, associations or ways of viewing the same information (elevator/accident/boss) in a more positive light under non-traumatic circumstances allows the brain, doing what it does best, to make new constructs of neurotransmitters in its natural effort to be as efficient, healthy and productive as possible at any given moment, to the extent the subject allows.

In one embodiment mixed with the feelings of being a survivor of the prior accident, and realizing they came through physical therapy quite well, the subject might also realize that they are not completely settled that the increased traffic is not a concern for the risk of another more serious accident. It is at that realization that the subject might start over at step 204 with "afraid of being injured in an accident on my commute," allowing the computer process to walk them through what negative memories and associations are raising that particular concern in them.

The example provided above illustrates an ideal circumstance and outcome, but, not every negative association is that simple to correct. However, once a subject experiences the process a handful of times, they tend to become more capable of seeing the connections to their anxiety, both cognitively and subconsciously, and can begin to reassociate experiences quite rapidly. According to an embodiment, a goal of the process is to reduce anxiety caused by unresolved or fearful prior experiences and to use the process to re-associated negative into positive, freeing the subject for higher levels of personal success.

As mentioned above, step 206 is a component of the program in which predefined performance hurdles or challenges are made available to the subject. If the subject finds themselves not knowing where to start, these can be used as primers to get the new subject started in the process. According to an embodiment, some of the categories available include Anxiety/Trauma, Depression, Grief/Loss/Betrayal, Relationships, Work/Life, Weight Loss/Health/Chronic Pain or Disease, Parenting, Sexual Identity, Sports, and Business/Financial, etc. Under each category the program provides numerous specifically theorized life challenges; for example, under Chronic Pain a challenge phrase might be "can't stop my chronic pain from keeping me home bound" or "I get angry when my partner doesn't understand my chronic pain" or finally, "I think my chronic pain is related to my depression."

Step 208, also mentioned above, is a tool allowing the subject to see predefined challenges on a randomized basis, pulling from the predefined categories in rapid fashion. According to an embodiment, this option includes: From the relationship category: general public sub-category, the program describes a hypothetical situation in which, while driving, the subject (vehicle 1) is cut off by another vehicle (vehicle 2). In response to the subjects tap on the horn as vehicle 2 drifts into their (vehicle 1) lane, the driver of vehicle 2 shouts an obscene remark or displays an obscene gesture. The challenge phrase options available to the subject might be; "The world today scares me," "I'm afraid of my anger towards strangers," "I can't control times of my own road rage," or "I can't relax when I drive." At this point the subject can modify one or all the options, save them to use in an iteration of the process at a future date, or request a complexly different challenge phrase. The program then asks the subject to identify a negative responsive emotion by providing a list that might include, for example, anger, trapped, failure, hate, fear, impatience, paranoia, etc., prompting the subject to continue with the process to the end.

FIGS. 3-17 are screen views of respective pages of a computer-based program 300, according to one embodiment. The program 300 is stored on a non-transitory computer-readable medium for implementation using a general-purpose computer, according to an embodiment. Each of the screen views of the program 300 are generated by the program in response to an action, or a series of actions by a user, via a user interface, during use of the program. The screen views of FIGS. 4-16 correspond to respective steps of an operation sequence of the program 300, i.e., a default sequence that the program will follow if a user simply advances according to onscreen prompts, and that will guide the user through an exercise that is intended to assist the user in taking or increasing control over troublesome aspects of the user's personality as a result of painful and/or negative prior experiences. However, during use, the user is typically free to navigate to other pages or views, and in particular may return to previous pages, to revise, for example, previous answers. The user may also repeat selected portions of the sequence from various pages as part of the process embodied by the program 300. Accordingly, although described here in a logical progression, operation of the program 300 or the operation sequence is not limited to the disclosed order of operation, nor are the claims limited to any particular order, including an order in which elements or steps are defined, unless such limitation is explicit in the claims. Furthermore, embodiments are contemplated in which additional pages are included and/or pages are omitted, or modified in scope or function, relative to the pages described here.

The program 300 is configured, in particular, for operation by a user via an internet connection. A user might, for example, launch the program 300 by selecting a link on the results page of an internet search engine, or on a mental health practitioner's web page, or on the web page of a mental health support group or hotline, etc.

Figure 3:
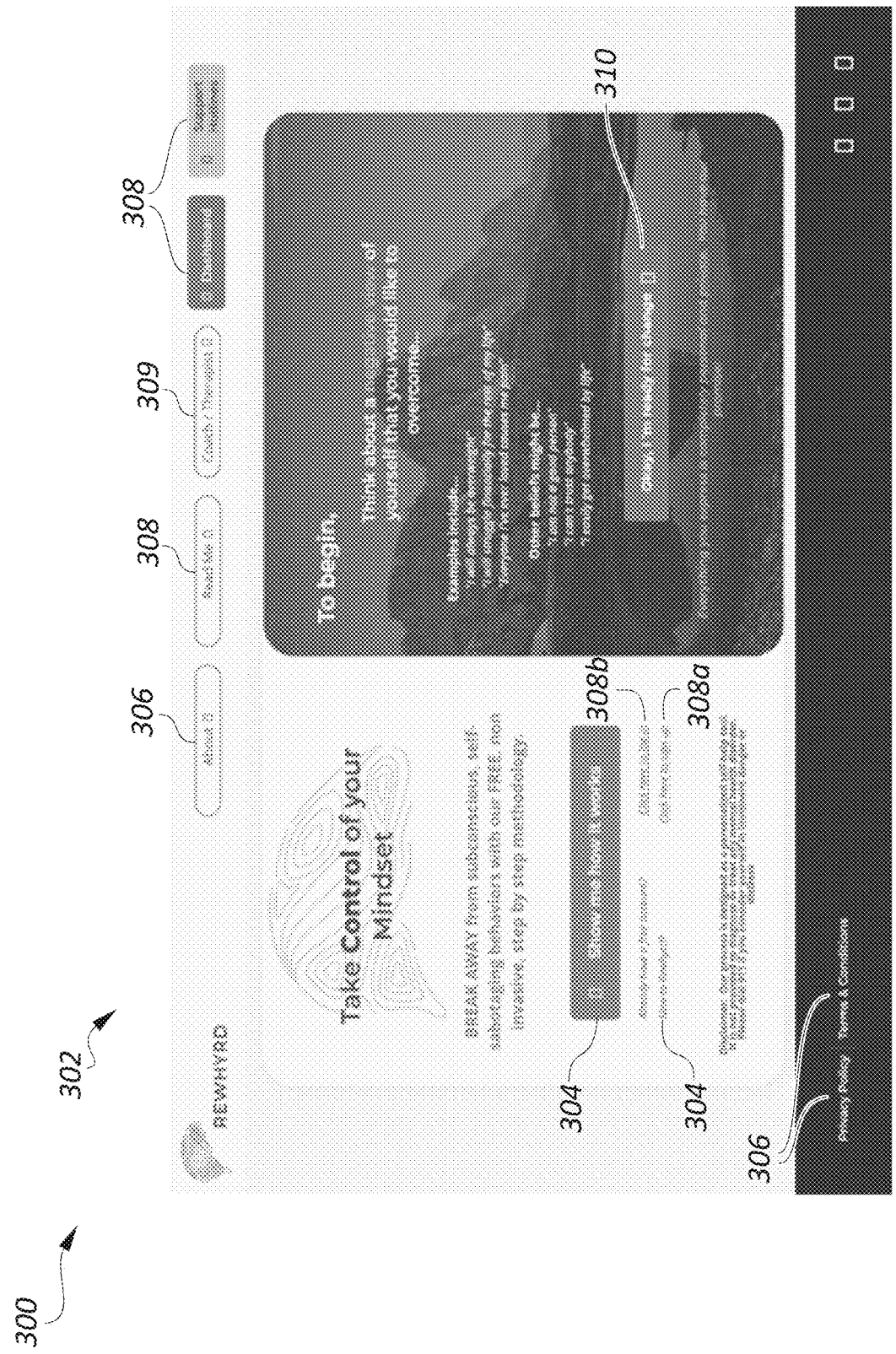
FIGS. 3-17 are screen views of respective pages of a computer-based program, according to an embodiment.

FIG. 3 is a screen view of a landing page 302 of the program 300, according to an embodiment. The landing page 302 is one page that may be opened when a user selects a link to the program 300 from another website, and is therefore usually the first page a user therapist/subject sees upon launching the program for the first time. Accordingly, the landing page 302 includes links 304 that a first-time user or visitor can follow for introductory information, as well as general information links 306 and links 308, 309 for internal navigation within or related to the program 300, including links 308a, 308b to pages where a user can create or modify an account or a registered user can log in to an existing account. For the convenience of the user, many of these links are included on others pages of the program. The contents of the pages to which the links 304-308 lead are largely self-explanatory, and, for the most part, peripheral to the primary operation of the program 300; they will therefore not be described in detail.

In one embodiment, selection of the Coach/Therapist link 309 opens a contact page where the user can establish a relationship with a coach, for example, who can assist the user in navigating the operation sequence, understanding the hoped-for result of the process, the underlying theory, etc. Additionally, or alternatively, the user can establish a relationship with a licensed therapist, who might, for example, help the user process feelings and impressions that arise during the process, etc. While the help of a coach or therapist might be very beneficial to the user, the link 309 is adjunct to, rather than an element of the operation sequence.

Figure 4:
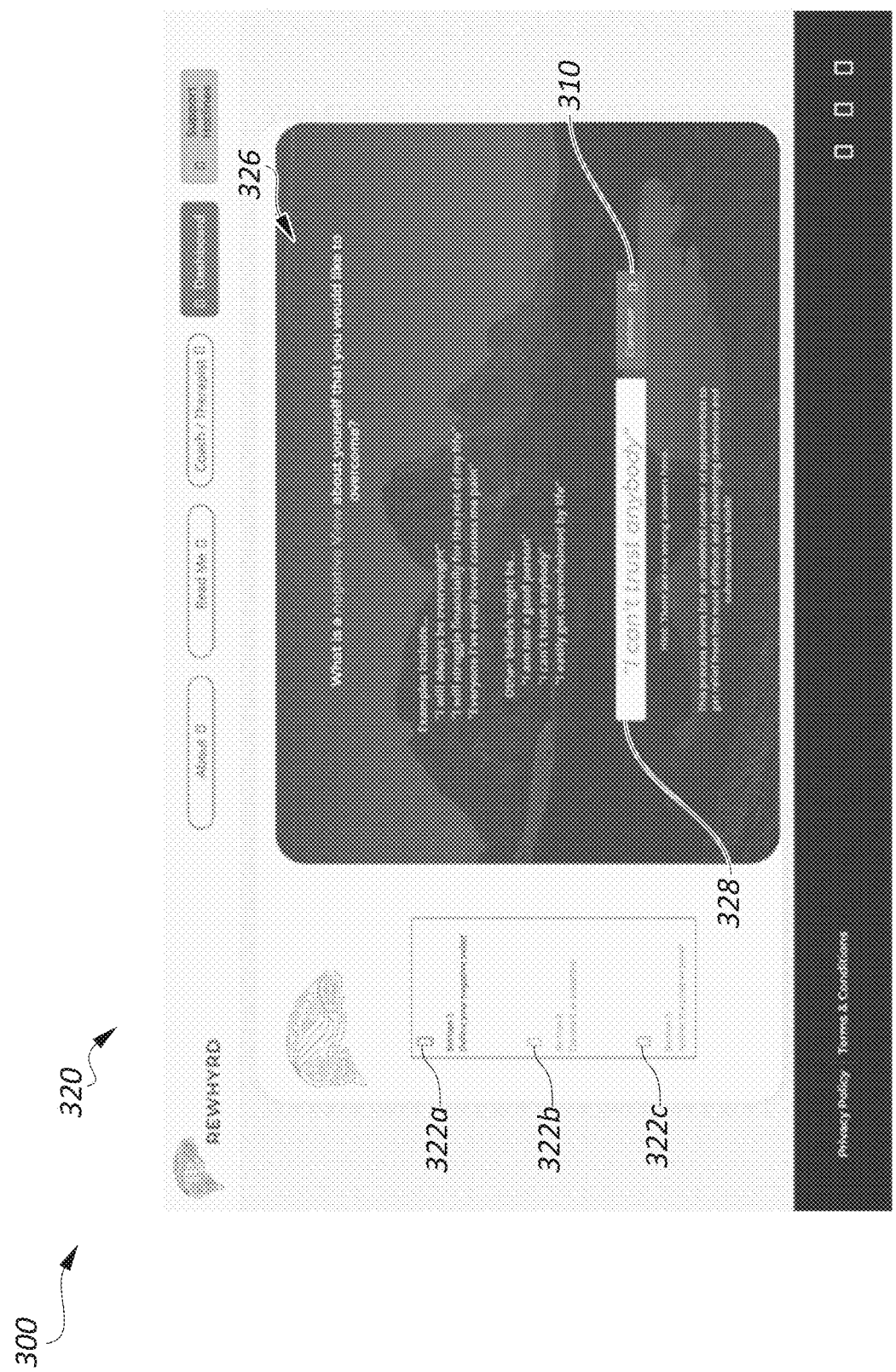

To initiate the operation sequence of the program 300 from the landing page 302, a user selects an Advance link 310, which links, in this case, to the first page in the sequence. FIG. 4 is a screen view of a first sequence page 320 of the program 300, according to an embodiment. Elements of the operation sequence can be grouped into a relatively smaller number of sections. In the embodiment shown, there are three sections: a Negative Belief section, a Positive Belief section, and an Anchor section. While performing tasks in the 535 Negative Belief section, the user identifies and examines personal beliefs, views, impressions, feelings, and/or responsive actions that produce net negative effects on or for the user. While performing tasks in the Positive Belief section, the user identifies and creates personal beliefs of views that reframe corresponding negative beliefs, reducing or eliminating the negative effects, and in many cases, producing net positive effects. While performing tasks in the Anchor section, the user anchors the positive beliefs so as to increase the user's resistance to reversion to the negative beliefs.

Most pages of the operation sequence include section links 322 that enable the user to skip to different sections of the operation sequence. The first sequence page 320 is the first page of the Negative Belief section of the sequence. Accordingly, if the user selects the Negative Belief section link 322a from another page in the sequence, the process will jump to the first sequence page 320. Likewise, selection of the Positive Belief section link 322b or the Anchor section link 322c will result in the process jumping to the first page of the corresponding section. Pages subsequent to the first sequence page 320 include a progress gauge 324 (see, e.g., FIG. 5) that shows the user's progress within each section of the operation sequence.

Instructions 326 on the first sequence page 320 prompt the user to identify a negative belief or view of himself that he would like to overcome. At various points in the operation sequence, the instructions text 326 may also include information that may be of interest to the user, such as, for example, helpful tips relating to completion of the various tasks, of the operation sequence, or about the underlying principles on which the sequence is based, etc. In the case of the first sequence page 320, as shown in FIG. 4, the instructions 326 include examples and suggestions for completing the task, such as might assist an inexperienced or first-time user on the first task of the sequence. According to an embodiment, the content of the instructions 326 is selected, in part, according to a level of experience of the particular user. Thus, if the user chooses later to repeat the operation sequence, identifying, for example, a different Negative View to work on, the instructions 326 may not include the same degree of "beginner" assistance, but may provide more in-depth information.

A text window 328 is provided, into which the user enters a self-selected negative 565 view. Upon completion, the user is prompted to select the Advance link 310, which advances the program 300 to the next page of the sequence.

Figure 5:
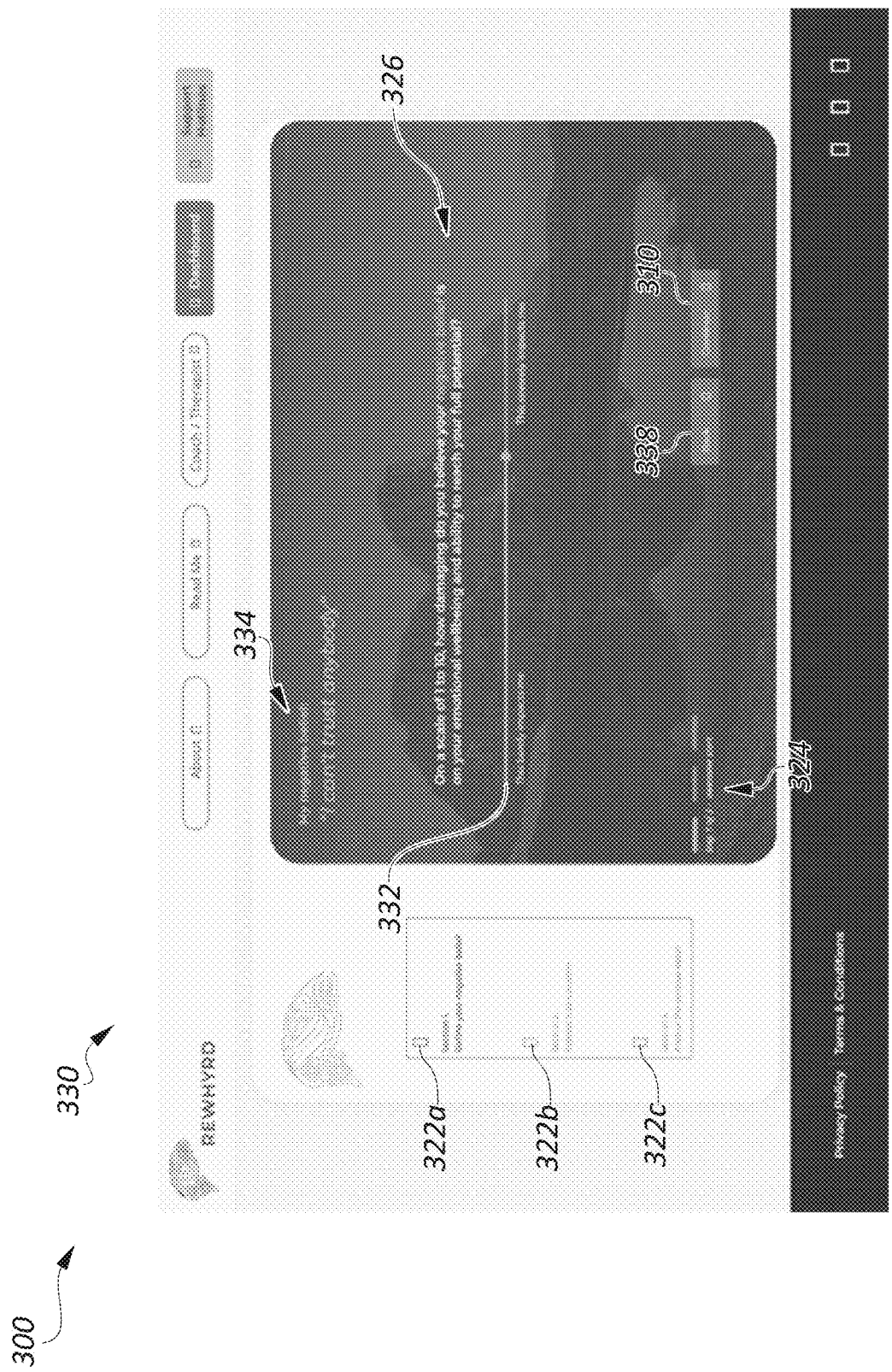

FIG. 5 is a screen view of a second sequence page 330 of the program 300, according to an embodiment. On the second sequence page 330, instructions 326 prompt the user to provide a rating as to how damaging the previously identified negative belief is to his wellbeing and ability to reach his full potential. The user moves a slider 332 to select a rating value. The negative belief that was identified on the preceding sequence page is shown at 336 for the user's reference. Completion of the task defined on the first and second sequence pages 320, 330 corresponds to the first of three steps that are part of the Negative Belief section, and is reflected in the Progress Gauge 324. The user can select the Advance link 310 to continue the sequence, or select the Back link 338 to move back to a previous sequence page, so as, for example, to review or revise the selected negative belief, or how it was articulated.

Figure 6:
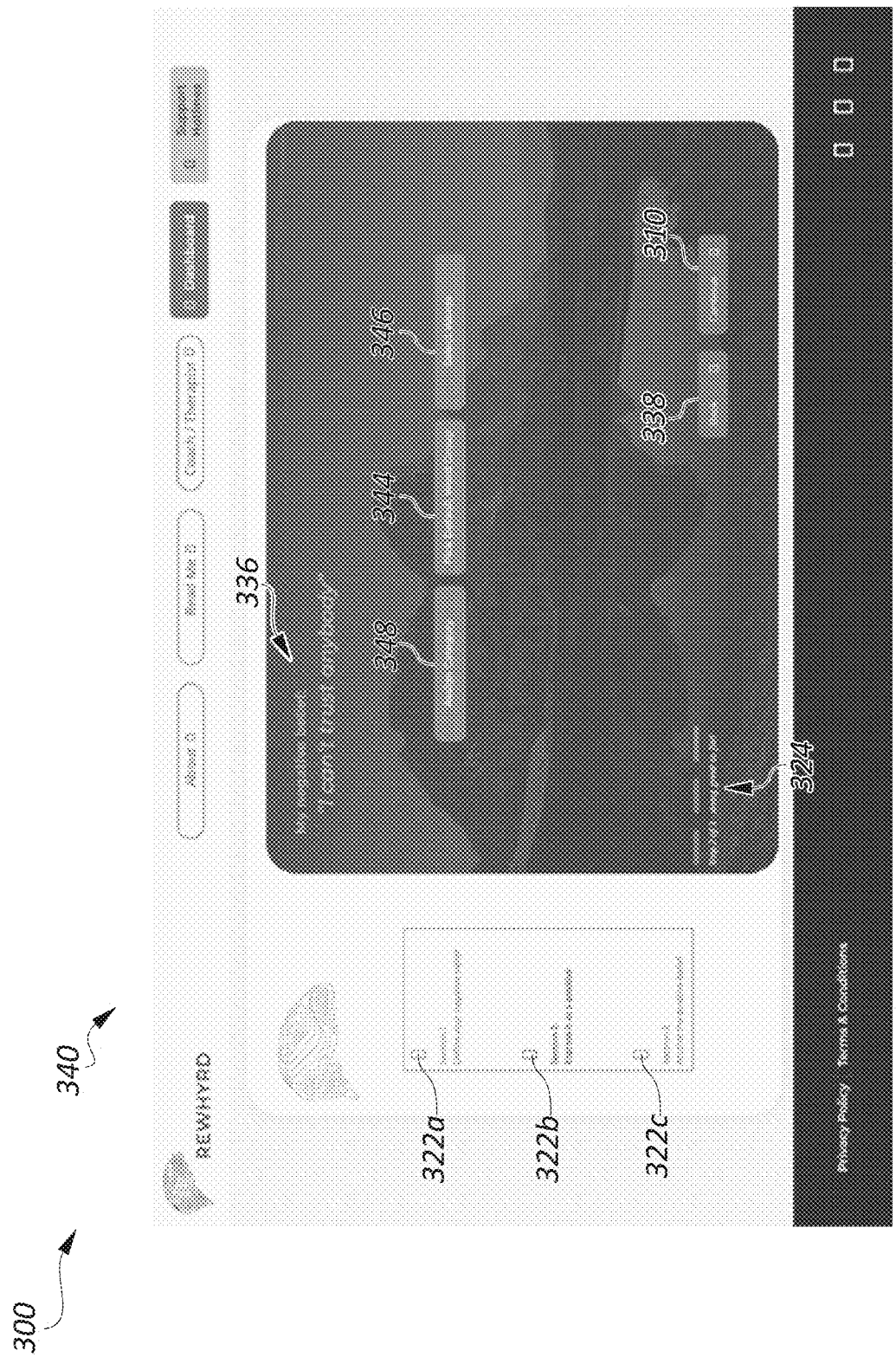

FIG. 6 is a screen view of a third sequence page 340 of the program 300, according to an embodiment. On the third sequence page 340, instructions 326 prompt the user to select three triggering words that seem, to the user, to strongly associate with, or trigger the selected negative belief. Using a Default Word Group link 344, the user has the option of selecting from among a predefined set of possible triggering words. Alternatively, the user can enter triggering words from any source, using the Select Words link 346. At a later page, the user will be encouraged to repeat the Negative Belief section while selecting a different set of words or a different negative belief. To simplify the word selection process, the user has the option of defining categories of words, using the Assign Category link 348. Once the three trigger words are selected, the user can advance to the next page of the sequence.

Figure 7:
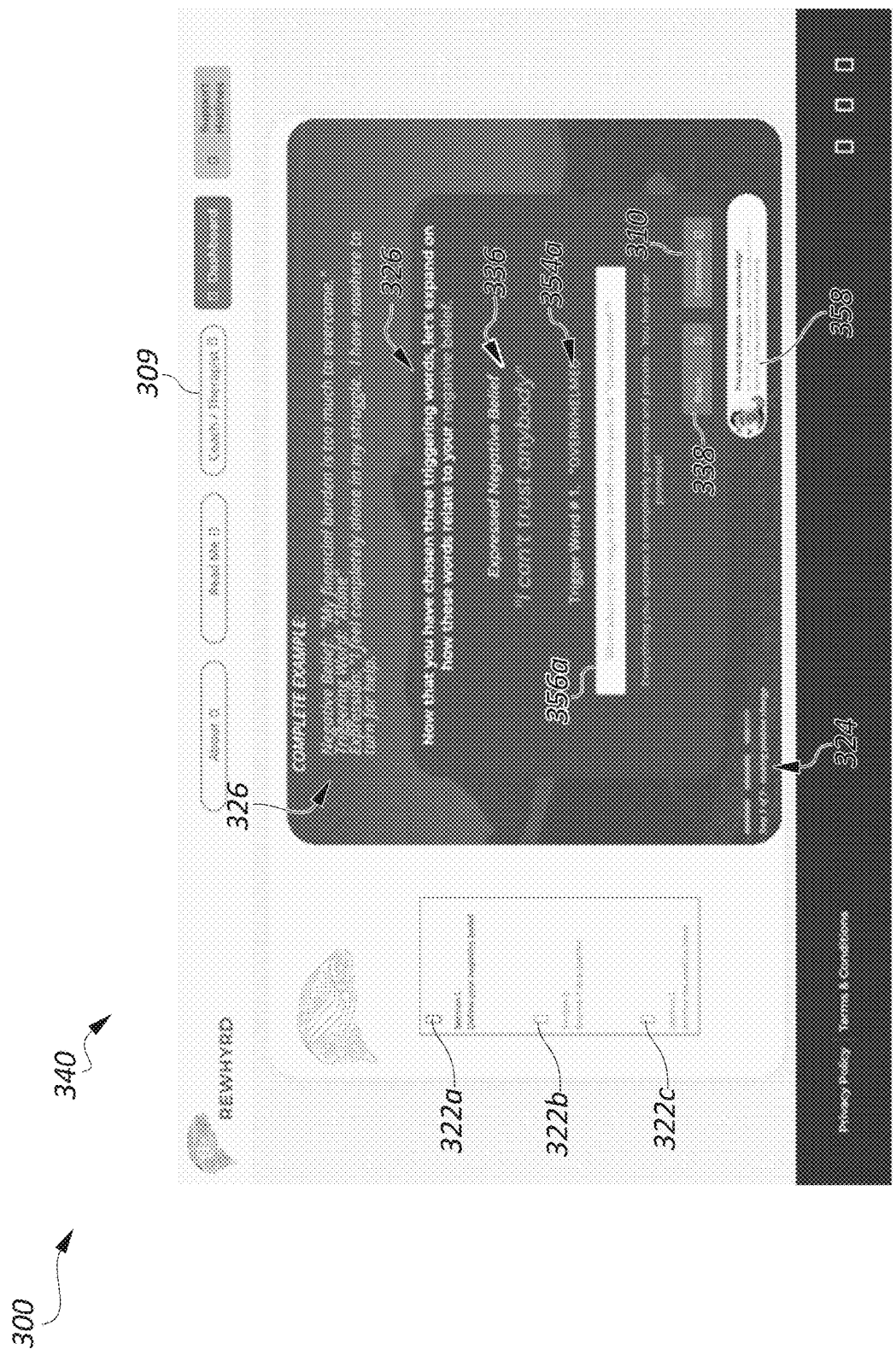
Figure 8:
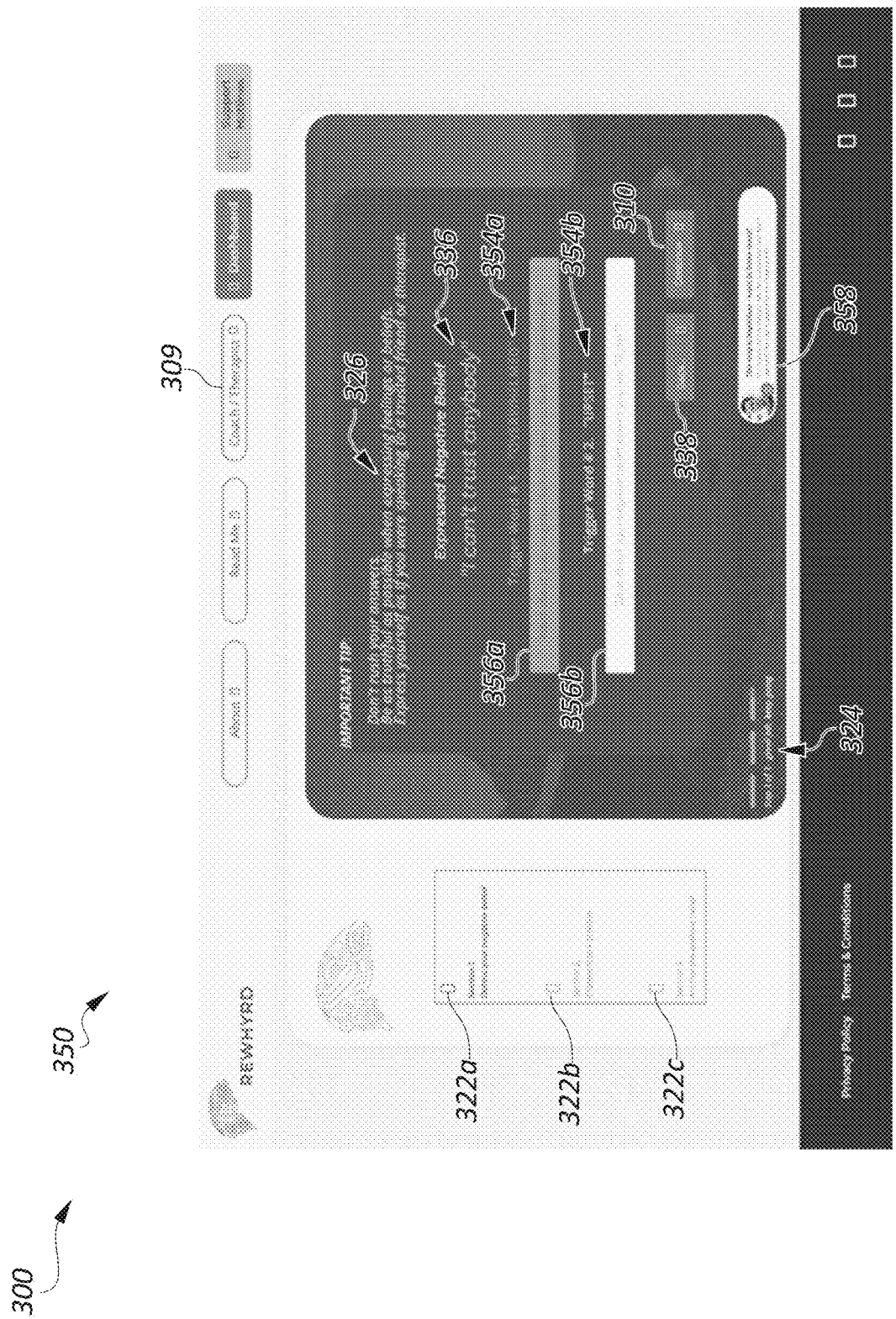
Figure 9:
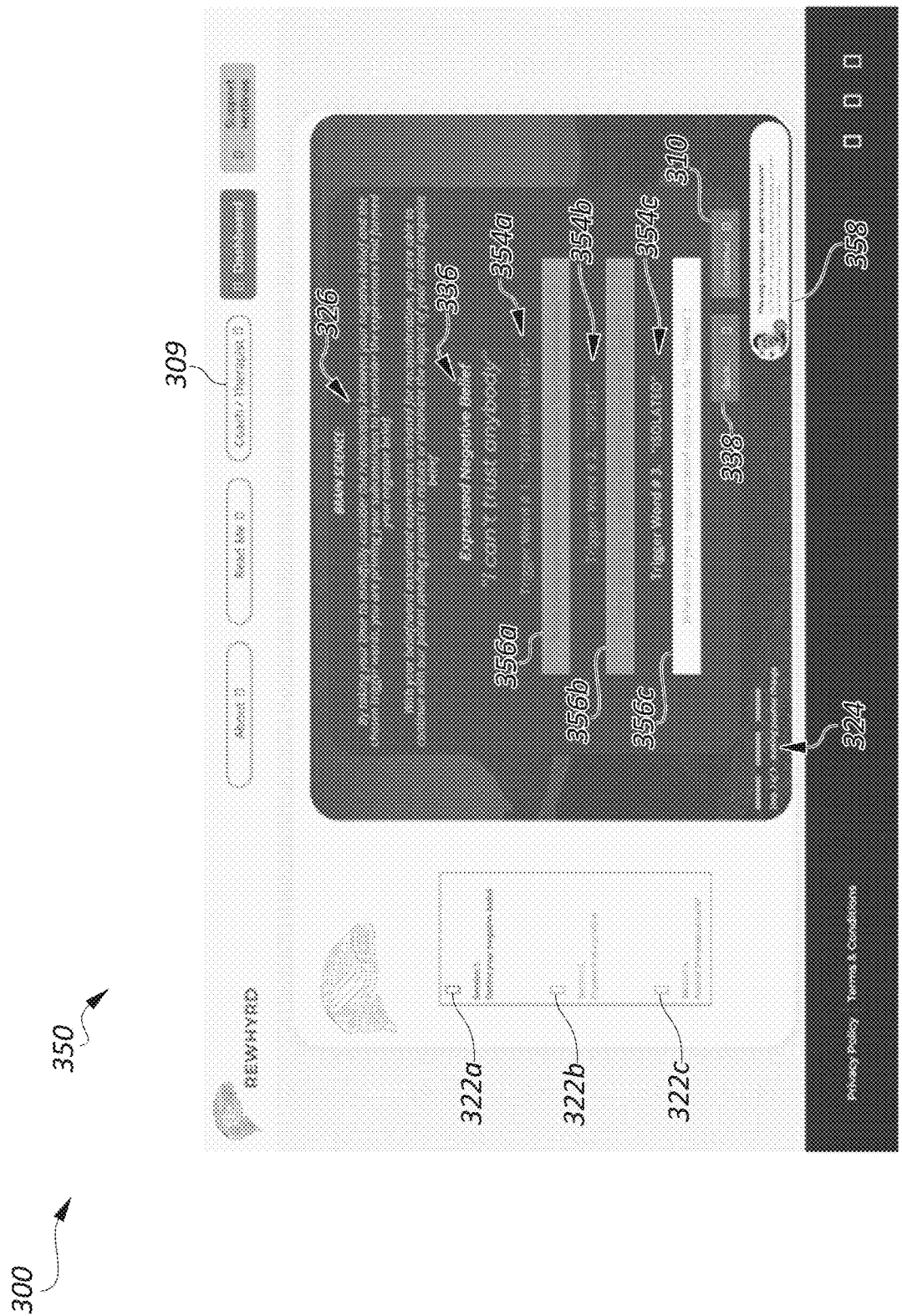

FIGS. 7-9 are progressive screen views of a fourth sequence page 350 of the program 300, according to an embodiment. Initially, as shown in FIG. 7, on the fourth sequence page 350, instructions 326 prompt the user to expand upon the selected triggering words, and how they relate to the selected negative belief. An example is provided at 326, a first one of the three selected triggering words is displayed at 354a, and a text box 356a is provided for the user to enter a response.

According to an embodiment, many of the pages include a Help link 358 that opens a chat window or a voice line, etc. with a process coach who can assist the user in completing the tasks of the operation sequence, and particularly, help the user understand what the program 300 is prompting for, and how to complete each task effectively. In general, selection of the Help link 358 is for assistance in the procedural aspects of the process, and will connect the user with an on-call process coach. In contrast, as described above with reference to FIG. 3, selection of the Coach/Therapist link 309 opens a contact page where the user can establish a relationship with a coach or therapist. In other words, according to an embodiment and to the extent practical, the contact page that is accessed by following the Coach/Therapist link 309 provides the tools for a user to communicate regularly with the same coach or therapist, and form a relationship that may give the user a higher degree of confidence in the assistance or advice provided.

When the user selects the Advance link 310 after expanding upon the first triggering word, the second of the three selected triggering words is displayed at 354b and a second text box 356b is provided, as shown in FIG. 8, for a response corresponding to the second word. Then, when the user again selects the Advance link 310 on the fourth sequence page 350, the third of the three selected triggering words is displayed at 354c and a third text box 356c is provided, as shown in FIG. 9, so that the user can enter a response corresponding to the third word. The task defined on the fourth sequence page 350 represents the final one of the three steps in the Negative Belief section, which is reflected in the progress gauge 324 as each of the three triggering words is dealt with.

Figure 10:
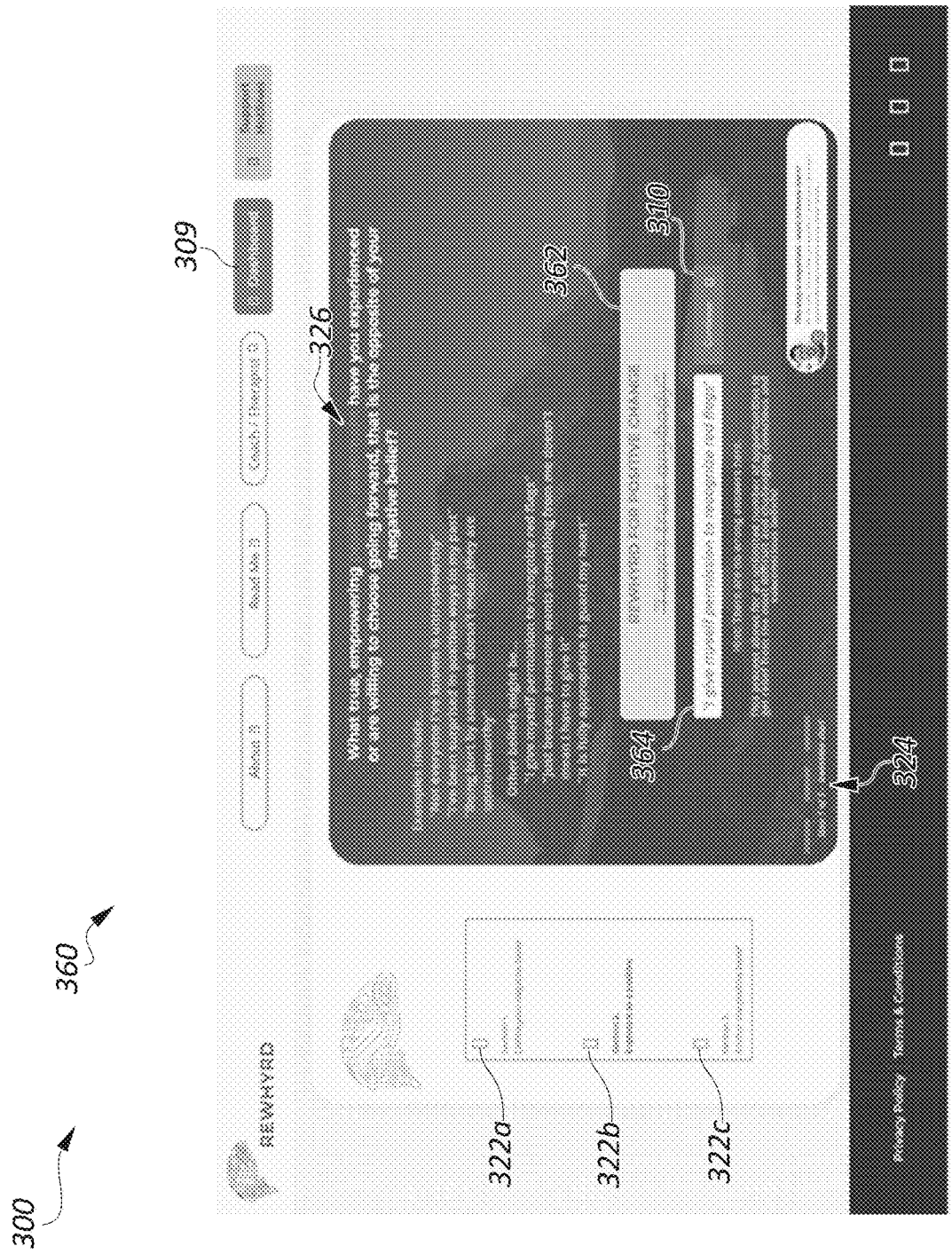

FIG. 10 is a screen view of a fifth sequence page 360 of the program 300, according to an embodiment. The fifth sequence page 360 is the first page of the Positive Belief section, which the user can move to from anywhere in the sequence by selecting the Positive Belief section link 322b. The pages of the Positive Belief section, shown in FIGS. 10-14, largely mirror, in a positive light, the pages of the Negative Belief Section, as shown in FIGS. 4-9. The instructions 326 on the fifth sequence page 360 prompt the user to identify a positive belief, also referred to as a Positive Reframe, that can oppose or replace the negative belief previously identified, and includes various examples to help the user. A text box 364 is provided for the user to enter the selected Positive Reframe, and the previously identified negative belief is shown struck through 362, suggesting that it has been deleted or overwritten. Upon completion of the task, the user is prompted to select the Advance link 310 to move to the next page.

Figure 11:

FIG. 11 is a screen view of a sixth sequence page 370 of the program 300, according to an embodiment. On the sixth sequence page 370, instructions 326 prompt No 630 instructions is an oversight the user to select three "reframing" words that seem, to the user, to strongly associate with, or enhance the selected positive belief. Using a Default Word Group link 372, the user has the option of selecting from among a predefined set of words. Alternatively, the user can enter any appropriate words, using the Select Words link 374, and can define or redefine word categories using the Reassign Category link 376. Once the three reframing words are selected, the user can advance to the next page of the sequence.

Figure 12:
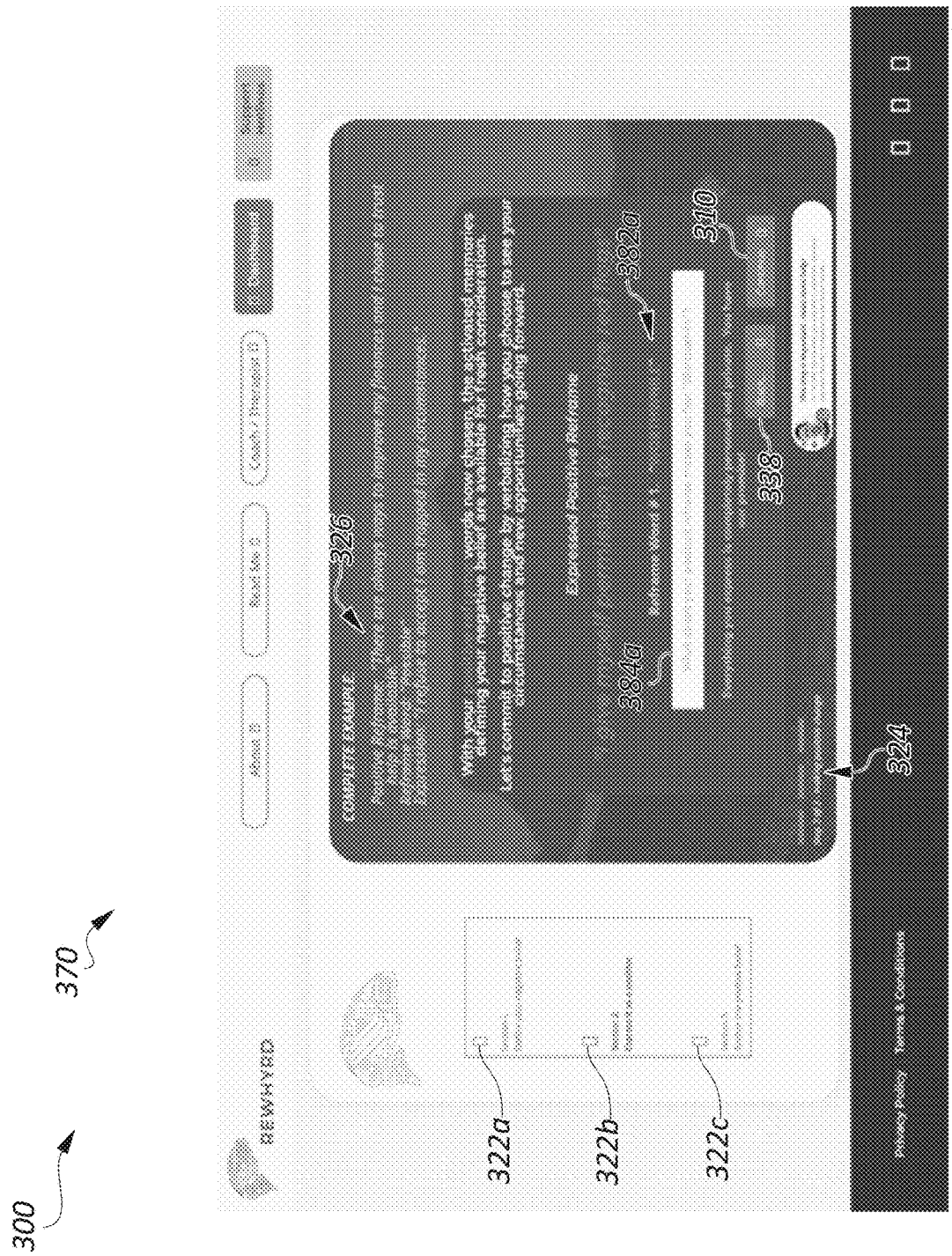
Figure 13:
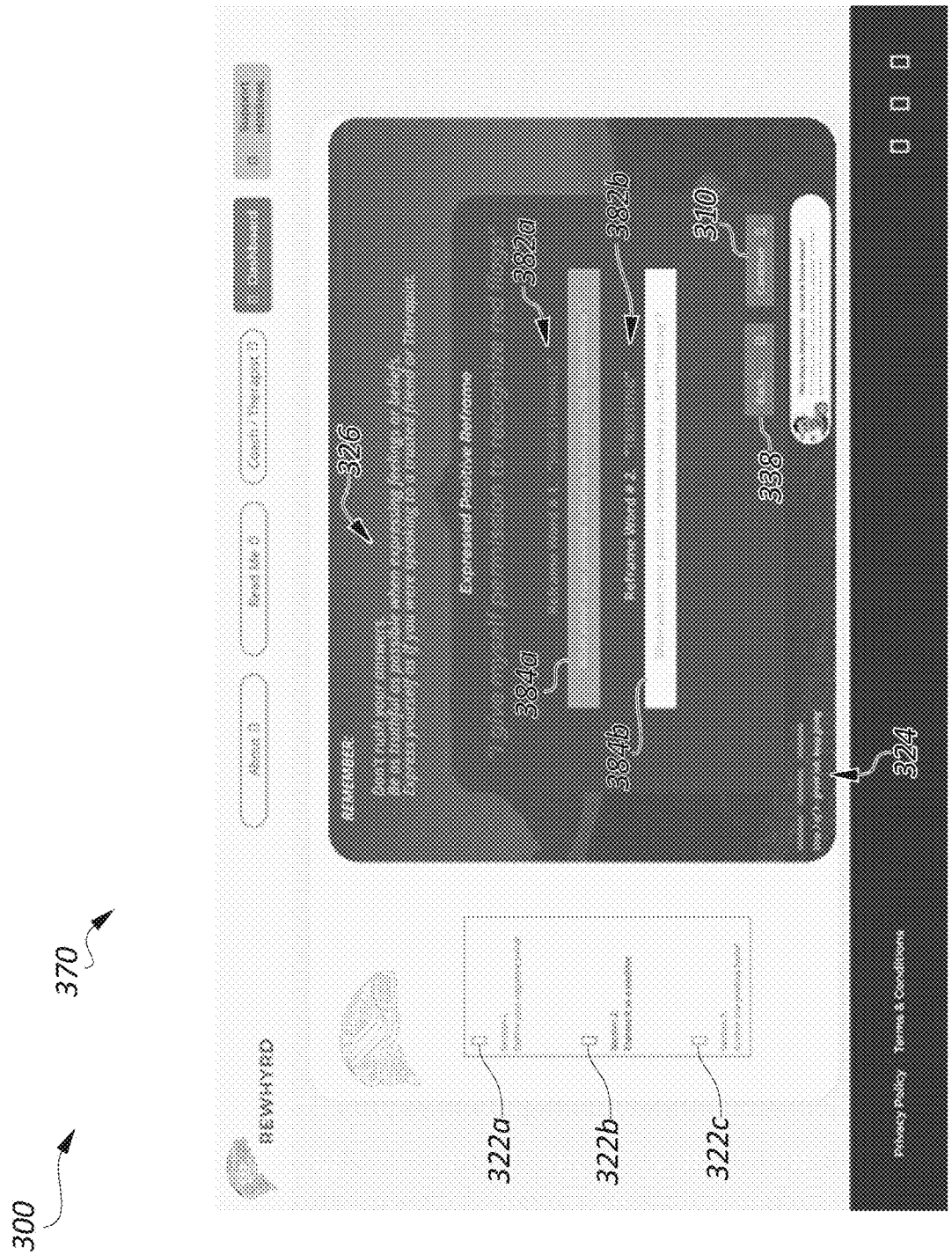
Figure 14:
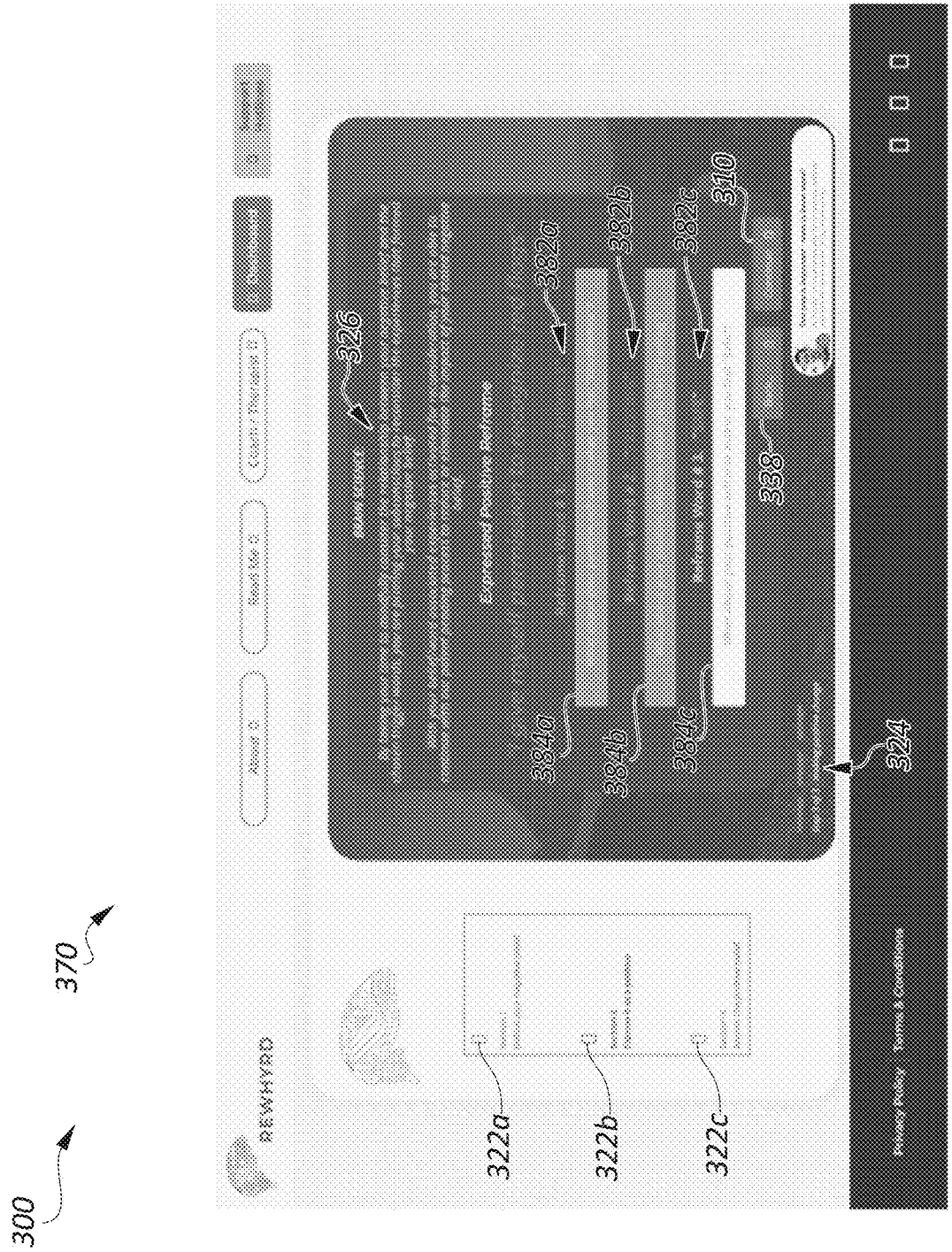

FIGS. 12-14 are progressive screen views of a seventh sequence page 380 of the program 300, according to an embodiment. Initially, as shown in FIG. 12, instructions 326 prompt the user to expand upon the selected reframing words, and how they relate to the selected Positive Reframe. Examples are also provided, a first one of the three selected Reframing Words is displayed, at 382a, and a text box 384a is provided for the user to enter a response.

When the user selects the Advance link 310, the second of the three selected reframing words is displayed at 382b and a second text box 384b is provided, as shown in FIG. 13, so that the user can provide a response corresponding to the second word. Then, when the user again selects the Advance link 310 on the seventh sequence page 380, the third of the three selected reframing words is displayed at 382*c* and a third text box 384*c* is provided, as shown in FIG. 14, so that the user can enter a response corresponding to the third reframing word.

Figure 15:
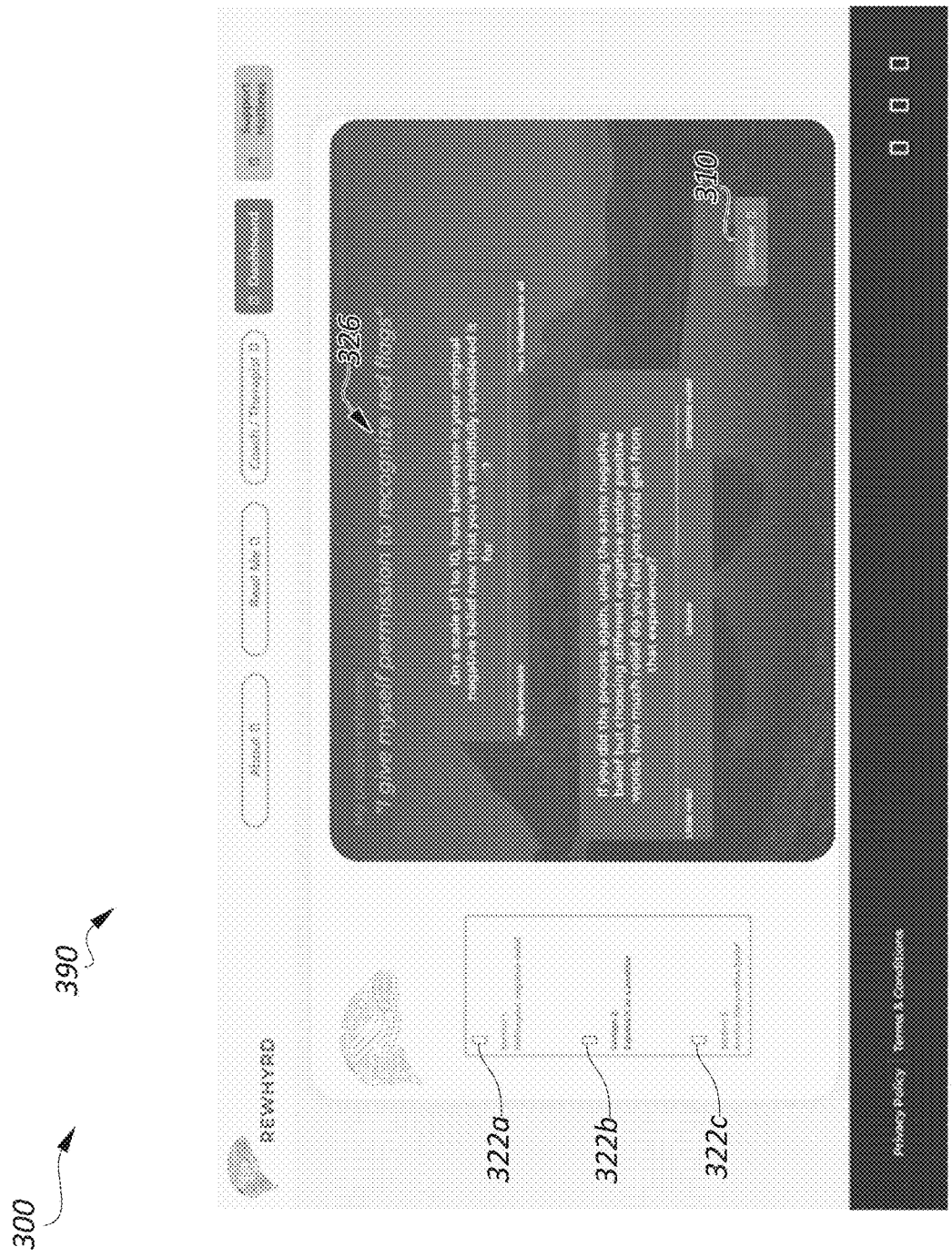

Upon completion of the task defined on the seventh sequence page 380, the user is prompted to select the Advance link, which opens an eighth operation sequence page 390, as shown in the screen view of FIG. 15. The eighth sequence page 390 is the first page of the Anchor section of pages of the operation sequence. Accordingly, selection of the Anchor Section link 322*c* from any page in the program will bring the user to this sequence page. On the eighth operation sequence page 390, the instructions 326 prompt the user to evaluate the strength of the negative belief that was identified on the first sequence page 320 of FIG. 4 in view of the tasks performed subsequent to the first sequence page, and in particular the reframing tasks of the sequence pages in the Positive Belief Section. The user operates a slider 392 to select a corresponding value. The user is also prompted to estimate, based on the results of the current iteration of the operation sequence, the level of relief he might experience by repeating the sequence with the same negative belief, but with a different set of three triggering words. A slider 394 is provided, on which the user selects a value that corresponds to the estimate. The user selects the Advance link 320 to advance to the next sequence page.

Figure 16:
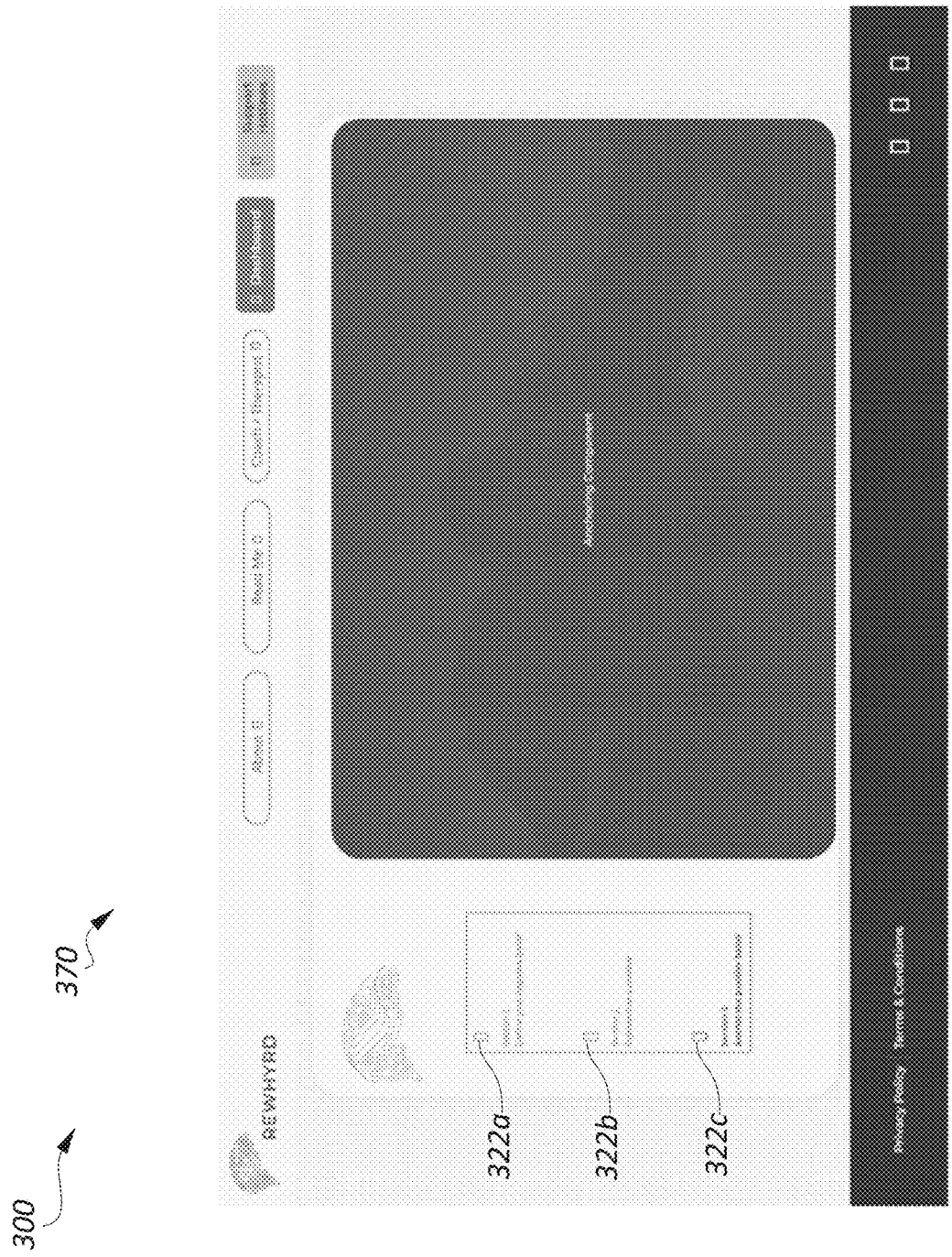
Figure 17:
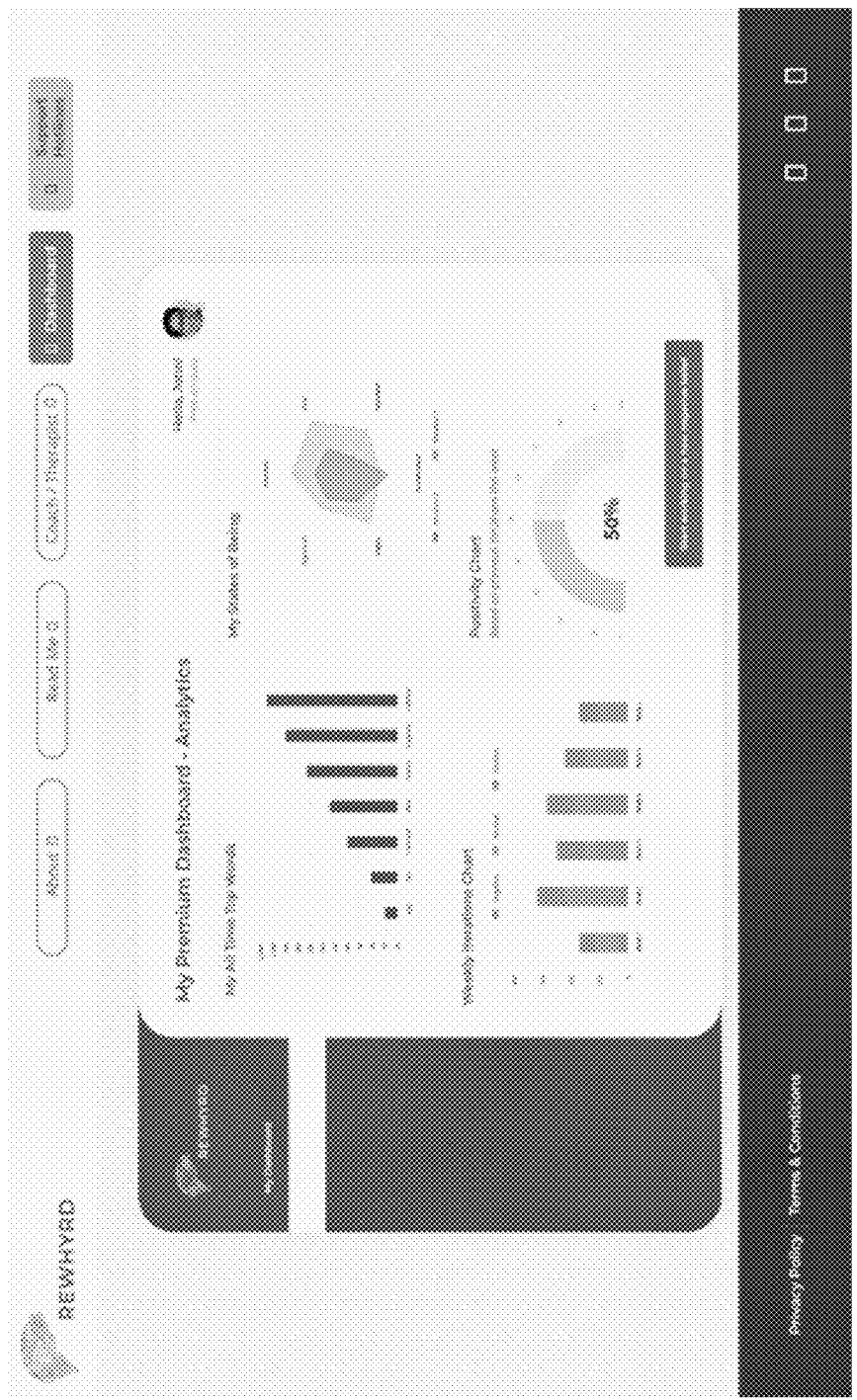

FIG. 16 is a screen view of a ninth sequence page 400 of the program 300, according to an embodiment. The ninth sequence page 400 is the final page of the operation sequence, and simply informs the user that he has completed to sequence. Instructions may be provided that provide suggestions for optimizing the results obtained in the just-completed sequence, for compounding those results through careful selection of negative beliefs and positives reframes in repeat iterations of the sequence, etc. opens an Analytics page 410, as shown in FIG. 17, that provides metrics relating to multiple iterations of the sequence by the user. For example, in the illustrated embodiment, shown a Words graph 412 lists the most frequently selected triggering and/or reframing words; a Performance graph 414 shows the cumulative effectiveness, by week, of the iterations of the sequence, based on the user's evaluation of each iteration; a Positivity chart 416 displays the current level of "positivity" for the current week, based on the user's input; and a States of Being Venn diagram 418 provides a comparison of the user's mental condition in a number of categories during multiple iterations of the sequence, etc.

The user can begin a new iteration of the operation sequence by selecting the Re-initiate link 420, which links to the first sequence page 320 of the operation sequence.

Over the course of the operation sequence, the user is encouraged to approach the tasks with deliberation and mindfulness. The strength of the positive effect of the program 300 on the user is generally directly related to the degree of thought and care with which the user approaches the process executed by the program. Accordingly, during an iteration of the operation sequence, as the user considers the tasks presented in light of previous responses, it is anticipated that the user may occasionally realize that a previous response could be refined or modified to enable a more apt or effective response at a later sequence page. Accordingly, not only is it appropriate for the user to return to an earlier sequence page, via the Back link 338 or one of the section links 322, the user may be instructed at various pages to review responses made at previous pages and think about whether any of the previous responses can be improved. Of course, with experience, a user will become more attuned to the operation sequence, and how to make best use of the process. The user may therefore be encouraged not only to repeat the process with a new negative belief in 695 order to assist in modifying other aspects of the user's response characteristics, but may also be encouraged to repeat the process with a previously-selected Negative Belief, in order to strengthen the effect as it related to the previously selected Negative Belief, particularly if the user finds that the effect of an iteration was lower than expected.

According to an embodiment, an operation sequence similar to that described above with reference to FIGS. 4-17 is available to users who obtain a paid registration, which gives such users full access to all of the features of the program 300. An alternative registration is available at no cost to users who wish to evaluate the efficacy of the program, or who do not wish to commit resources, etc. A free registration provides access to a somewhat limited version of the operation sequence. For example, with a free registration, a user may be required to select triggering words and reframing words from specific lists of words, may be limited in the number of iterations that can be performed within a selected period, may have limited access to coaches or therapists, or may be required to pay fees for various kinds of access, etc. Additionally, marketing pages may be presented during iterations of the operation sequence encouraging a user with a free registration to upgrade to a paid registration.

In referring to a user or a subject, the description may use gendered pronouns, such as he or she, his or hers, etc. This is for clarity and simplicity, only; where gender-specific terms are used to refer to a user or a subject, such terms are to be understood as referring broadly to any user or subject, without regard to the gender or gender identity of the individual.

Figure 18:
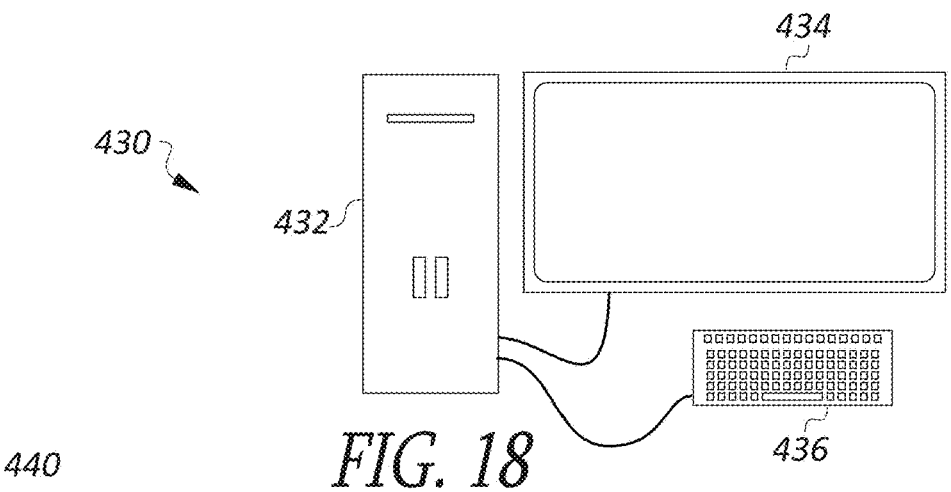
FIG. 18 is a diagrammatic view of a general-purpose computer and peripherals configured to display the pages of the program of FIGS. 3-17, according to an embodiment 45.

FIG. 18 is a diagrammatic view of a general-purpose computer system 430 configured to display the sequence pages of the program of FIGS. 3-17, according to an embodiment. The computer system 430 includes a tower 432, a display screen 434, and a keyboard 436. The computer system is configured to access the internet, such as via an ethernet connection or a WiFi connection. Although depicted as a desktop-type system with the display 434 and keyboard 436 shown as peripheral components coupled to the tower, the computer system 430 can, alternatively, be differently configured, such as a laptop computer, tablet, smart phone, etc., any of which can be used to operate the program 300, according to respective embodiments.

Figure 19:
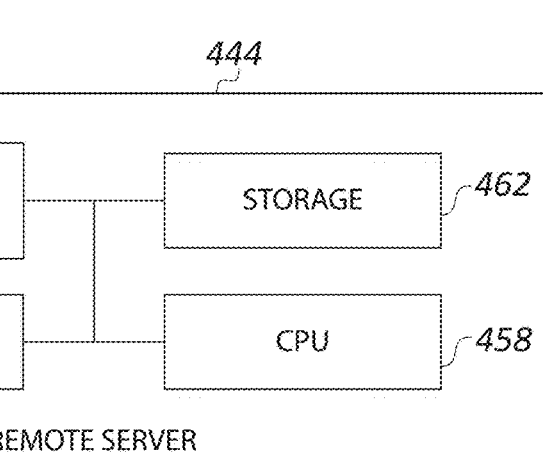
FIG. 19 is a block diagram of a computer system configured to store and/or execute the program of FIGS. 3-17, according to an embodiment.
Figure 19:
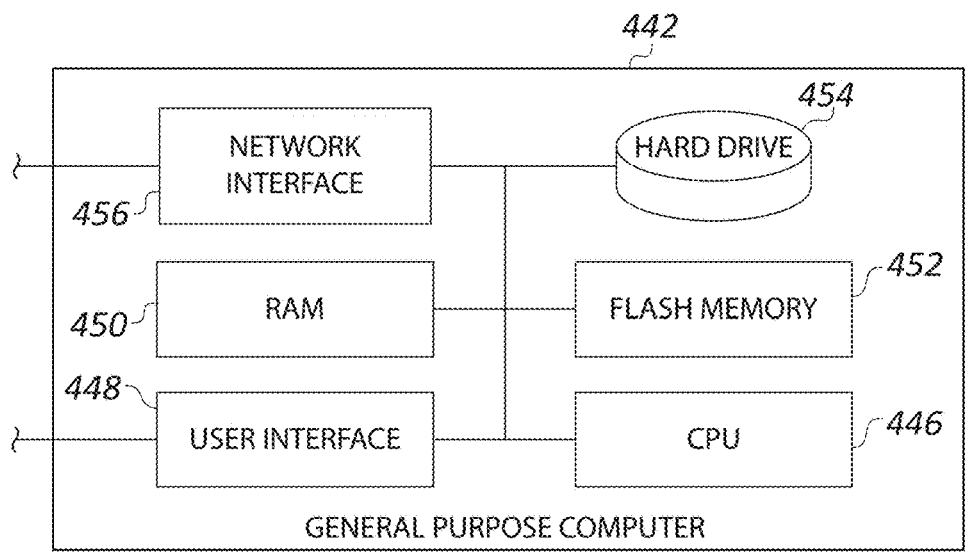

FIG. 19 is a block diagram of a computer system 440 configured to store and/or execute the program 300 of FIGS. 3-17, according to an embodiment. The system 440 includes a general purpose computer 442 and remote server 444. The computer 442 includes a CPU 446, a user interface 448, random access memory 450, a flash memory 452, a hard drive 454, and a network interface 456. The remote server 444 includes a CPU 458, random access memory 460, data storage 462, and a network interface 464.

A person having ordinary skill in the art will recognize that a typical computer system may include components that are not shown here in detail, such as, e.g., a power supply, a battery, circuit boards, extensive cabling, etc. Such components are well understood, and a person with ordinary skill will completely understand which components may be necessary or useful according to the type of system and the desired capabilities. Thus, the components that are shown are primarily those that might be employed to execute the instructions embodied by a program such as the program 300 of FIGS. 3-17. In fact, even those components are well enough understood in the art that any details provided here are only by way of example. Some of the components shown can be omitted or other components can be substituted, as will be readily understood by a person having ordinary skill in the art. For example, a flash memory 452 and a hard drive 454 are both shown as components of the computer 442. However, it is well understood that some personal computing devices, such as desktop and laptop computers commonly use hard drives for data storage, while other devices, including, e.g., tablets and smart phones, commonly use flash memories for data storage. Other devices may employ both for different types of storage.

Similarly, the remote server 444 is shown where in some embodiments the program is stored remotely from the computer(s) that run the program. In embodiments in which the program is stored in permanent memory of the computer on which the program will be launched, there is no requirement for remote storage or network access.

According to an embodiment, a program is stored in the permanent, nonvolatile data storage 462 of the remote server 444. The program may, for example, include instructions for performing a process similar to the process 200 of FIG. 2, or may be similar to the program 300 described with reference to FIGS. 3-17. The server 444 is coupled to the internet via the network interface 464. The general-purpose computer 442 is also coupled to the internet, via the network interface 456. To launch the program, A user directs operation of the computer 442 via the user interface 448, which may include, or be operatively coupled with, e.g., a video display screen, a keyboard, a mouse or touchpad, a microphone, audio speakers, etc. Via the network interface 464, the user navigates to and selects a link associated with the program, or identifies and selects the program from a menu or file listing, etc. This may be via an internet connection, a LAN network connection, or any other appropriate connection means.

When the user selects the program, this signals to the server 444 to transmit the program to the computer. The program may be transmitted in its entirety to the computer 765 442, or the server 444 may transmit portions of the program as they are required. Under some circumstances, such as when a user purchases a copy of the program, the computer 442 may store a permanent copy of the program in its own data storage, e.g., the hard drive 454 or the flash memory 452. Alternatively, the computer may store the transmitted data in its RAM. If the program is stored in the permanent memory, the program or portions 770 thereof are extracted from the memory and saved in the RAM. Thus, in either case, the program is launched from the RAM. Most modern computing devices have sufficient RAM to hold the entire program, which is preferable, inasmuch as the user may choose to perform the program steps out of order, or to repeat portions, etc., which could result in slow operation if it were necessary for the CPU to retrieve instructions for individual process steps as they are required. When the program is launched, the CPU 446 of the computer 442 controls the operation of the computer in accordance with the instructions that are part of the program, so as to present the appropriate images on the video display, and permit the user to navigate through the environment of the program, provide the appropriate responses, etc.

In embodiments in which users register at a particular website to obtain access to the program, the website may also collect data relating to each user's interaction with the program. The collected data may be saved on the server 444, or may be saved elsewhere. Where such user data is collected, it is likely that users of the program will be sensitive about the security of their data. According to an embodiment, the website and user data storage site are protected by a security program, such as is known in the art, to protect the user data from access, theft, or corruption by unauthorized parties.

As used herein, the term negative belief refers also to negative feelings, negative views, negative behaviors, and negative responses to selected or specific external stimuli. Conversely, positive belief refers also to positive feelings, views, behaviors, and responses to selected or specific external stimuli.

Where a claim uses the term personal, this refers to an individual who performs an action or process step defined in the corresponding limitation of the claim. So for example, if a claim includes a limitation reciting identifying a personal negative belief, this means that the negative belief is personal to the individual who is identifying the belief. Inasmuch as the qualitative values positive and negative are, in this context, subjective to the individual who is identifying the belief, the ultimate determination of the quality of any particular belief, positive or negative, is made by the individual.

In many of the drawings, elements are designated with a reference number followed by a letter, e.g., "322*a*, 322*b*." In such cases, the letter designation is used where it may be 800 useful in the corresponding description to differentiate between or to refer to specific ones of a number of otherwise similar or identical elements. Where the description omits the letter from a reference, and refers to such elements by number only, this can be understood as a general reference to any or all of the elements identified by that reference number, unless other distinguishing language is used.

Ordinal numbers, e.g., first, second, third, etc., are used in the claims according to conventional claim practice, i.e., for the purpose of clearly distinguishing between claimed elements or features thereof, etc., without limiting those elements by other defining language. Ordinal numbers may be assigned arbitrarily, or assigned simply in the order in which elements are introduced. The use of such numbers does not suggest any other relationship, such as order of operation, relative position of such elements, etc. Furthermore, an ordinal number used to refer to an element in a claim should not be assumed to correlate to a number used in the specification to refer to an element of a disclosed embodiment on which that claim reads, nor to numbers used in unrelated claims to designate similar elements or features.

The abstract of the present disclosure is provided as a brief outline of some of the principles of the invention according to one embodiment, but is not intended as a complete or definitive description of any single embodiment thereof, nor should it be relied upon to define terms used in the specification or claims. The abstract does not limit the scope of the claims.

It will be understood that the scope of the appended claims should not be limited by particular embodiments set forth herein but should be construed in a manner consistent with the specification as a whole.

What is claimed is:

1. A method for modifying a user's personal tendency to respond negatively to selected stimuli, the method comprising the steps of:
   the user identifying a first negative personal belief;
   the user correlating the first negative personal belief with each of at least one negative terms, wherein the at least one negative terms provokes respective personal emotional responses when associated with the first negative personal belief;

the user identifying and recording the respective personal emotional responses provoked by the association of each of the plurality of negative terms with the first negative personal belief;

the user identifying a positive personal belief as an alternative to the first negative personal belief;

the user correlating the positive personal belief with each of a plurality of positive terms that provoke the respective personal emotional responses when associated with the positive personal belief; and the user identifying and recording the respective personal emotional responses provoked by the association of each of the plurality of positive terms with the positive personal belief.

2. The method of claim 1, comprising the step of:

the user evaluating a degree of impact on the first negative personal belief produced by performance of the steps listed in claim 1.

3. The method of claim 1, comprising the step of:

the user repeating the steps listed in claim 1.

4. The method of claim 3, wherein the step of identifying a first negative personal belief comprises a step of the user identifying a second negative personal belief that is different from the first negative personal belief.

5. The method of claim 3, comprising the step of identifying a third negative personal belief that is the same as the first negative personal belief.

6. The method of claim 5, wherein the step of correlating the second negative personal belief with at least one negative terms comprises a step of the user correlating the second negative personal belief with at least one of the at least one negative term that provoke respective personal emotional responses from the user when associated with the second negative personal belief.

7. The method of claim 1, further comprising the steps of:

the user re-iterating the steps listed in claim 1;

following each iteration of the steps listed in claim 1, the user evaluating the efficacy of the corresponding iteration;

recording data derived from the evaluating the efficacy following each iteration of the steps listed in claim 1.

8. The method of claim 7, comprising a step of:

based on the data recorded of recording data derived from the evaluating the efficacy following each iteration of the steps listed in claim 1, tracking personal progress with respect to effectively modifying the first negative personal belief.

9. The method of claim 1, wherein the first negative personal belief comprises a reflexive negative personal response to selected stimuli, and the positive personal belief comprises a positive personal behavior selected to supplant the first negative personal response to the selected stimuli.

10. The method of claim 1 wherein each of at least one negative terms, and each of a plurality of positive terms consists of a single word.

11. A method for modifying a user's personal tendency to respond negatively to selected stimuli utilizing a software program resident on a non-transient, computer-readable medium the software configured for modifying personally undesirable behaviors and beliefs, the software program comprising: recorded instructions configured to control a digital computing device to perform a set of process steps; the method comprising the steps of:

the software program prompting the user to identify a first negative personal belief;

the user identifying the first negative personal belief;

the software program prompting the user to correlate the first negative personal belief with at least one negative term that provokes respective personal emotional responses when associated with the first negative personal belief;

the user correlates the first negative personal belief with the at least one negative term;

the software program prompting the user to identify and record the respective personal emotional responses provoked by the association of each of the plurality of negative terms with the first negative personal belief;

the software program prompting the user to identify a positive personal belief as an alternative to the first negative personal belief;

the user identifying the positive personal belief as an alternative to the first negative personal belief the software program prompting the user to correlate the positive personal belief with each of a plurality of positive terms that provoke respective personal emotional responses when associated with the positive personal belief;

the user correlating the positive personal belief with each of a plurality of positive terms that provoke respective personal emotional responses when associated with the positive personal belief;

the software program prompting the user to identify and record the respective personal emotional responses provoked by the association of each of the plurality of positive terms with the positive personal belief; and the user to identifying and record the respective personal emotional responses provoked by the association of each of the plurality of positive terms with the positive personal belief.

12. The method as recited in claim 11, comprising the step of:

the software program prompting the user to evaluate a degree of impact on the first negative personal belief produced by performance of the steps of claim 11.

13. The method of claim 11, comprising the steps of:

repeating the steps listed in claim 11.

14. The method as recited in claim 13, wherein the step of the software program prompting the user to identify a second negative personal belief comprises a step of the software program prompting the user to identify a second negative personal belief that is different from the first negative personal belief.

15. The method as recited in claim 13, wherein the step of the software program prompting the user to identify a second negative personal belief comprises a step of the software program prompting the user to identify the second negative personal belief that is the same as the first negative personal belief.

16. The method as recited in claim 15, wherein the step of the software program prompting the user to correlate the negative personal belief with each of a plurality of negative terms comprises a step of the software program prompting the user to correlate the second negative personal belief with each of a different plurality of negative terms that provoke respective personal emotional responses when associated with the negative personal belief, in which each of the different plurality of negative terms is different from all of the negative terms of the plurality of negative terms.

17. The method of claim 11, further comprising the steps of:
- repeating the steps listed in claim 11;
- following each iteration of the steps of claim 11, the software program prompting the user to evaluate the efficacy of the corresponding iteration;
- recording data derived from reports by the user regarding the efficacy following each iteration of the steps of claim 11.

18. The method of claim 17, comprising the step of:
- based on the data recorded in the step of recording data derived from reports by the user regarding the efficacy following each iteration of the steps of claim 11, the user tracking personal progress of the user with respect to effectively modifying negative personal beliefs.

19. The method of claim 11, wherein the identified first negative personal belief comprises a reflexive negative response by the user to selected stimuli, and the positive personal belief comprises a positive behavior of the user selected by the user to supplant the negative response to the selected stimuli.

20. The method of claim 11 wherein each of at least one negative terms, and each of a plurality of positive terms consists of a single word.

\* \* \* \* \*